(12) United States Patent
Lazzari et al.

(10) Patent No.: US 7,109,259 B2
(45) Date of Patent: Sep. 19, 2006

(54) PIPERAZINONE DERIVATIVES

(75) Inventors: Dario Lazzari, Casalecchio di Reno (IT); Mirko Rossi, San Lazzaro di Savena (IT); Graziano Zagnoni, Vergato (IT); Alessandro Zedda, Casalecchio di Reno (IT); Stephen Mark Andrews, New Fairfield, CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 626 days.

(21) Appl. No.: 10/138,986

(22) Filed: May 3, 2002

(65) Prior Publication Data

US 2003/0027902 A1     Feb. 6, 2003

Related U.S. Application Data

(63) Continuation of application No. 09/443,074, filed on Nov. 18, 1999, now abandoned.

(30) Foreign Application Priority Data

Nov. 24, 1998  (EP) .................... 98811160

(51) Int. Cl.
C08K 5/3452  (2006.01)
C08K 5/3492  (2006.01)
C07D 403/14  (2006.01)

(52) U.S. Cl. ............... 524/90; 524/100; 544/198

(58) Field of Classification Search ........... 544/198; 524/90, 100

See application file for complete search history.

(56) References Cited

U.S. PATENT DOCUMENTS

| | | | | |
|---|---|---|---|---|
| 4,240,961 A | 12/1980 | Lai | ............. | 260/239.3 |
| 4,297,497 A | 10/1981 | Lai | ............. | 544/384 |
| 4,466,916 A | 8/1984 | Lai et al. | ............. | 260/239.3 |
| 4,480,092 A | 10/1984 | Lai et al. | ............. | 544/113 |
| 4,629,752 A | 12/1986 | Layer et al. | ............. | 524/100 |
| 4,639,479 A | 1/1987 | Lai et al. | ............. | 524/100 |
| 4,650,870 A | 3/1987 | Conetta et al. | ............. | 544/357 |
| 4,665,185 A | 5/1987 | Winter et al. | ............. | 546/184 |
| 4,753,979 A | 6/1988 | Conetta et al. | ............. | 524/100 |
| 4,841,053 A | 6/1989 | Son et al. | ............. | 544/384 |
| 4,929,653 A | 5/1990 | Kletecka et al. | ............. | 524/96 |
| 5,013,836 A | 5/1991 | Lai | ............. | 540/512 |
| 5,278,209 A * | 1/1994 | Kletecka et al. | ............. | 524/100 |
| 5,310,771 A | 5/1994 | Walters | ............. | 524/100 |

FOREIGN PATENT DOCUMENTS

| | | |
|---|---|---|
| EP | 0001559 | 5/1979 |
| EP | 0189877 | 8/1986 |
| EP | 0448037 | 9/1991 |
| EP | 0828195 | 3/1998 |
| EP | 0867467 | 9/1998 |
| EP | 0900823 | 3/1999 |
| WO | 88/08863 | 11/1988 |
| WO | 92/04404 | 3/1992 |

OTHER PUBLICATIONS

Chem. Abstr. 109:129838 for JP 63086711 (1988).

* cited by examiner

Primary Examiner—Tae H. Yoon
(74) Attorney, Agent, or Firm—Shiela A. Loggins

(57) ABSTRACT

A compound of the formula (I)

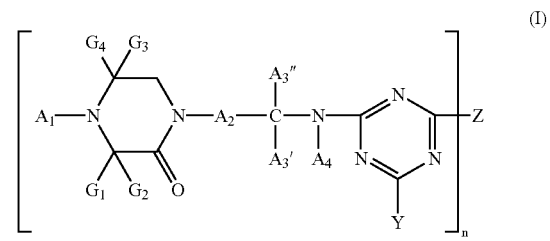

wherein
n is preferably 3;
$G_1$, $G_2$, $G_3$ and $G_4$ are independently of one another e.g. $C_1$–$C_4$alkyl;
$A_1$ is e.g. hydrogen or methyl;
$A_2$ is e.g. methylene;
$A_3'$ and $A_3''$ are e.g. $C_1$–$C_4$alkyl;
$A_4$ is e.g. $C_1$–$C_8$alkyl;
Y is e.g. a group of the formula (IV)

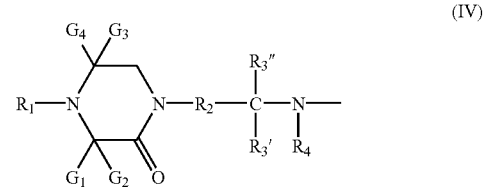

wherein $R_1$ is e.g. hydrogen or methyl, $R_2$ is e.g. methylene, $R_3'$ and $R_3''$ are e.g. $C_1$–$C_4$alkyl and $R_4$ is e.g. hydrogen or $C_1$–$C_8$alkyl; and
Z is e.g. a group of the formula (VI)

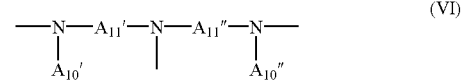

with $A_{10}'$ and $A_{10}''$ being independently of one another e.g. hydrogen or $C_1$–$C_4$alkyl and $A_{11}'$ and $A_{11}''$ being independently of one another e.g. $C_2$–$C_6$alkylene,
is useful for stabilizing an organic material against degradation induced by light, heat or oxidation.

12 Claims, No Drawings

PIPERAZINONE DERIVATIVES

This Application is a continuation of application Ser. No. 09/443,074, filed Nov. 18, 1999, now abandoned.

This invention relates to piperazinone derivatives, to an organic material susceptible to light, heat or oxidation, containing a piperazinone derivative and to a method for stabilizing such an organic material. This invention further relates to intermediate products.

Several piperazinone derivatives and their use as stabilizers are described, for example, in U.S. Pat. No. 4,240,961, U.S. Pat. No. 4,480,092, U.S. Pat. No. 4,629,752, U.S. Pat. No. 4,639,479, U.S. Pat. No. 5,013,836, U.S. Pat. No. 5,310,771 and WO-A-88/08863.

The present invention relates in particular to a compound of the formula (I)

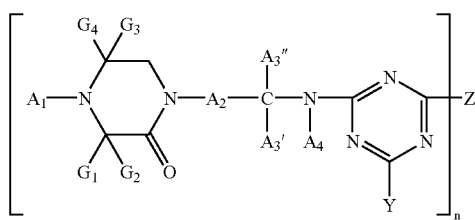

wherein n is an integer from 1 to 4;

$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

$A_1$ is hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl;

$A_2$ is $C_2$–$C_{14}$alkylene or a group —CA$_2'$(A$_2''$)- with A$_2'$ and A$_2''$ being independently of one another hydrogen, $C_1$–$C_{18}$alkyl or $C_5$–$C_{12}$cycloalkyl;

$A_3'$ and $A_3''$ are independently of one another hydrogen, $C_1$–$C_{18}$alkyl, $C_2$–$C_{18}$alkyl interrupted by oxygen; or $C_5$–$C_{12}$cycloalkyl;

$A_4$ is hydrogen, $C_1$–$C_{18}$alkyl, $C_2$–$C_{18}$hydroxyalkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_{12}$phenylalkyl which is unsubstituted or substituted on the phenyl by 1, 2 or 3 $C_1$–$C_4$alkyl; tetrahydrofurfuryl, a group of the formula (II),

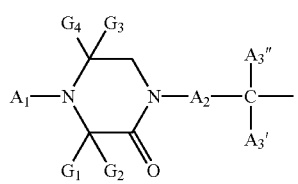

wherein $A_1$, $A_2$, $A_3'$ and $A_3''$ are as defined above;

or $C_2$–$C_4$alkyl which is substituted in the 2, 3 or 4 position by $C_1$–$C_8$alkoxy, di($C_1$–$C_4$alkyl)amino or a group of the formula (III);

with L being —O—, —CH$_2$—, —CH$_2$CH$_2$— or >N—CH$_3$;

Y is —OA$_5$, —SA$_5$, —N(A$_6$)(A$_7$) or a group of the formula (IV);

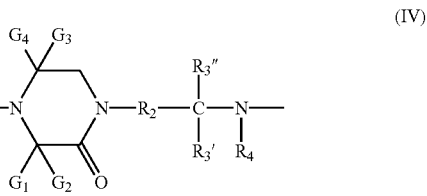

wherein $R_1$ has one of the definitions given above for $A_1$, $R_2$ has one of the definitions given above for $A_2$, $R_3'$ and $R_3''$ have independently of one another one of the definitions given above for $A_3'$ and $A_3''$, and $R_4$ has one of the definitions given above for $A_4$;

$A_5$, $A_6$ and $A_7$ are independently of one another hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_{12}$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by $C_1$–$C_8$alkoxy, di($C_1$–$C_4$alkyl)amino or a group of the formula (III), and $A_5$ is additionally a group of the formula (II), or —N(A$_6$)(A$_7$) is additionally a group of the formula (III);

when n is 1, Z is —OA$_5$, —SA$_5$, —N(A$_6$)(A$_7$) or a group of the formula (IV) as defined above;

when n is 2, Z is a group of the formula (V)

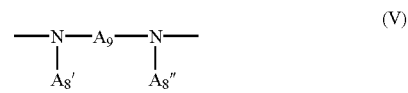

wherein $A_8'$ and $A_8''$ are independently of one another hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl;

$C_7$–$C_{12}$phenylalkyl which is unsubstituted or substituted on the phenyl by 1, 2 or 3 $C_1$–$C_4$alkyl;

tetrahydrofurfuryl, a group of the formula (II) or $C_2$–$C_4$alkyl which is substituted in the 2, 3 or 4 position by —OH, $C_1$–$C_8$alkoxy, di($C_1$–$C_4$alkyl)amino or a group of the formula (III);

$A_9$ is $C_2$–$C_{14}$alkylene, $C_4$–$C_{14}$alkylene interrupted by oxygen or sulphur; $C_5$–$C_7$cycloalkylene, $C_5$–$C_7$cycloalkylenedi($C_1$–$C_4$alkylene), $C_1$–$C_4$-alkylenedi($C_5$–$C_7$cycloalkylene) or phenylenedi($C_1$–$C_4$alkylene);

when n is 3, Z is a group of the formula (VI)

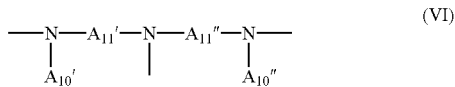

wherein
$A_{10}'$ and $A_{10}''$ have independently of one another one of the definitions of $A_8'$ and $A_8''$; and
$A_{11}'$ and $A_{11}''$ have independently of one another one of the definitions of $A_9$;
when n is 4, Z is a group of the formula (VII)

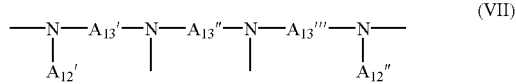

wherein
$A_{12}'$ and $A_{12}''$ have independently of one another one of the definitions of $A_8'$ and $A_8''$; and
$A_{13}'$, $A_{13}''$ and $A_{13}'''$ have independently of one another one of the definitions of $A_9$;
the radicals $A_1$, the radicals $A_2$, the radicals $A_3'$, the radicals $A_3''$, the radicals $A_4$ or the radicals Y have independently of one another the same meaning or a different meaning and the repeating units of the formula

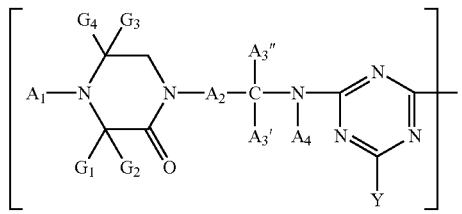

being present in the compound of the formula (I) are identical or different;
with the proviso that in at least one group of the formula

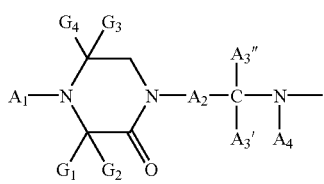

$A_4$ is different from hydrogen and $-(A_3')C(A_3'')-$ is different from methylene.

A further embodiment of the present invention is a compound of the formula (I-1)

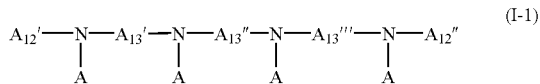

with A being a group of the formula

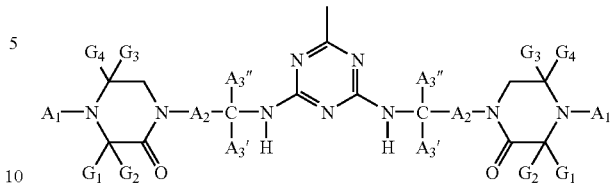

wherein
$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;
$A_1$ is $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{15}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl;
$A_2$ is $C_2$–$C_{14}$alkylene or a group —CH$_2$—;
$A_3'$ and $A_3''$ are independently of one another $C_1$–$C_{18}$alkyl;
$A_{12}'$ and $A_{12}''$ are independently of one another hydrogen or $C_1$–$C_4$alkyl;
$A_{13}'$, $A_{13}''$ and $A_{13}'''$ are independently of one another $C_2$–$C_{14}$alkylene; and
the radicals $G_1$, the radicals $G_2$, the radicals $G_3$, the radicals $G_4$, the radicals $A_1$, the radicals $A_2$, the radicals $A_3'$ or the radicals $A_3''$ are independently of one another identical or different.

Also an embodiment of this invention is a compound of the formula (I-2)

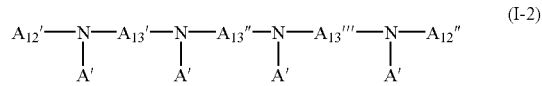

with A' being a group of the formula

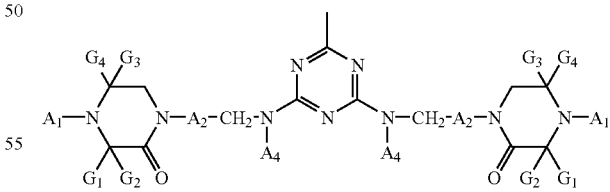

wherein
$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;
$A_1$ is hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{15}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —$CH_2CH(OH)(G)$ with G being hydrogen, methyl or phenyl;

$A_2$ is $C_2$–$C_{14}$alkylene or a group —$CH_2$—;

$A_4$ is $C_1$–$C_{18}$alkyl or $C_2$–$C_{18}$hydroxyalkyl;

$A_{12}'$ and $A_{12}''$ are independently of one another hydrogen or $C_1$–$C_4$alkyl;

$A_{13}'$, $A_{13}''$ and $A_{13}'''$ are independently of one another $C_2$–$C_{14}$alkylene; and the radicals $G_1$, the radicals $G_2$, the radicals $G_3$, the radicals $G_4$, the radicals $A_1$, the radicals $A_2$ or the radicals $A_4$ are independently of one another identical or different.

This invention relates also to compounds of the formula (I-3)

$$A_{12}'\!\!-\!\!\underset{\underset{A''}{|}}{N}\!\!-\!\!A_{13}'\!\!-\!\!\underset{\underset{A''}{|}}{N}\!\!-\!\!A_{13}''\!\!-\!\!\underset{\underset{A''}{|}}{N}\!\!-\!\!A_{13}'''\!\!-\!\!\underset{\underset{A''}{|}}{N}\!\!-\!\!A_{12}'' \qquad \text{(I-3)}$$

with A″ being a group of the formula

[structure diagram showing piperidinone ring with substituents $G_1$, $G_2$, $G_3$, $G_4$, $A_1$ on nitrogen, linked via $A_2$ to carbon bearing $A_3'$, $A_3''$, connected to triazine ring with substituent Y and NH]

wherein $G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

$A_1$ is hydrogen, $C_1$–$C_{18}$alkyl, oxyl, —OH, —$CH_2CN$, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{15}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —$CH_2CH(OH)(G)$ with G being hydrogen, methyl or phenyl;

$A_2$ is $C_2$–$C_{14}$alkylene or a group —$CH_2$—;

$A_3'$ and $A_3''$ are independently of one another $C_1$–$C_{18}$alkyl;

Y is —$N(C_1$–$C_{18}$alkyl$)_2$;

$A_{12}'$ and $A_{12}''$ are independently of one another hydrogen or $C_1$–$C_4$alkyl;

$A_{13}'$, $A_{13}''$ and $A_{13}'''$ are independently of one another $C_2$–$C_{14}$alkylene; and the radicals $G_1$, the radicals $G_2$, the radicals $G_3$, the radicals $G_4$, the radicals $A_1$, the radicals $A_2$, the radicals $A_3'$, the radicals $A_3''$ or the radicals Y are independently of one another identical or different.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$G_1$, $G_2$, $G_3$ and $G_4$ are preferably $C_1$–$C_4$alkyl, in particular methyl.

One of the preferred meanings of $A_1$ and $R_1$ is $C_1$–$C_4$alkyl, in particular methyl.

One of the preferred meanings of $A_3'$, $A_3''$, $R_3'$ and $R_3''$ is $C_1$–$C_8$alkyl, in particular $C_1$–$C_4$alkyl for example methyl.

One of the preferred meanings of $R_4$, $A_4$, $A_5$, $A_6$ and $A_7$ is $C_1$–$C_8$alkyl.

An example of $C_2$–$C_{18}$hydroxyalkyl and of $C_2$–$C_4$alkyl substituted by —OH is 2-hydroxyethyl.

Examples of $C_2$–$C_{18}$alkyl interrupted by oxygen and of $C_2$–$C_4$alkyl substituted by $C_1$–$C_8$alkoxy, preferably by $C_1$–$C_4$alkoxy, in particular methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$–$C_4$alkyl substituted by di($C_1$–$C_4$alkyl)amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

The group of the formula (III) is preferably

[morpholine structure: —N(CH$_2$CH$_2$)$_2$O]

Preferred examples of $C_2$–$C_4$alkyl substituted by a group of the formula (III) are groups of the formula

[Y—N(piperazine)—(CH$_2$)$_{2-4}$—]. The group [O—N(morpholine)—(CH$_2$)$_{2-4}$—]

is particularly preferred.

Examples of alkenyl containing not more than 18 carbon atoms are allyl, 2-methylallyl, butenyl, hexenyl, undecenyl and octadecenyl. Alkenyls in which the carbon atom in the 1-position is saturated are preferred, and allyl is particularly preferred.

An example of $C_3$–$C_8$alkynyl is 2-butynyl.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_6$–$C_{12}$Alkoxy, in particular heptoxy and octoxy, is one of the preferred meanings of $A_1$ and $R_1$.

Examples of acyl containing not more than 8 carbon atoms are formyl, acetyl, propionyl, butyryl, pentanoyl, hexanoyl, heptanoyl, octanoyl, acryloyl, methacryloyl and benzoyl. $C_1$–$C_8$Alkanoyl, $C_3$–$C_8$alkenyl and benzoyl are preferred. Acetyl and acryloyl are especially preferred.

Examples of $C_1$–$C_{18}$alkanoyloxy are formyloxy, acetyloxy, propionyloxy, butyryloxy, pentanoyloxy, hexanoyloxy, heptanoyloxy and octanoyloxy.

Examples of ($C_1$–$C_{18}$alkoxy)carbonyl are methoxycarbonyl, ethoxycarbonyl, propoxycarbonyl, butoxycarbonyl, pentyloxycarbonyl, hexyloxycarbonyl, heptyloxycarbonyl and octyloxycarbonyl.

Examples of $C_5$–$C_{12}$cycloalkyl which is unsubstituted or substituted by 1, 2 or 3 $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted $C_5$–$C_8$cycloalkyl, in particular cyclohexyl, is preferred.

Examples of $C_5$–$C_{12}$cycloalkoxy are cyclopentoxy, cyclohexoxy, cycloheptoxy, cyclooctoxy, cyclodecyloxy, cyclododecyloxy and methylcyclohexoxy. $C_5$–$C_8$Cycloalkoxy, in particular cyclopentoxy and cyclohexoxy, is preferred.

Examples of phenyl substituted by 1, 2 or 3 $C_1$–$C_4$alkyl or $C_1$–$C_4$alkoxy are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_{12}$phenylalkyl which is unsubstituted or substituted on the phenyl by 1, 2 or 3 $C_1$–$C_4$alkyl or $C_1$–$C_4$alkoxy are benzyl, methylbenzyl, dimethylbenzyl, trimethylbenzyl, t-butylbenzyl, 2-phenylethyl and methoxybenzyl. $C_7$–$C_9$phenylalkyl, in particular benzyl, is preferred.

Example of $C_7$–$C_{12}$phenylalkoxy unsubstituted or substituted on the phenyl by 1, 2 or 3 $C_1$–$C_4$alkyl or $C_1$–$C_4$alkoxy are benzyloxy, methylbenzyloxy, dimethylbenzyloxy, trimethylbenzyloxy, t-butylbenzyloxy, 2-phenylethyloxy and methoxybenzyloxy. $C_7$–$C_9$phenylalkoxyl, in particular benzyloxy, is preferred.

Examples of alkylene containing not more than 14 carbon atoms are ethylene, propylene, trimethylene, tetramethylene, pentamethylene, hexamethylene, octamethylene, decamethylene and dodecamethylene. $A_9$, $A_{11}'$, $A_{11}''$, $A_{13}'$, $A_{13}''$ and $A_{13}'''$ are preferably independently of one another $C_2$–$C_{10}$alkylene, especially $C_2$–$C_8$alkylene or $C_2$–$C_6$alkylene. $C_2$–$C_4$alkylene is particularly preferred.

$A_2$ as a group —$CA_2'(A_2'')$— is preferably methylene.

Examples of $C_4$–$C_{14}$alkylene interrupted by —O— or —S—, e.g. 1, 2 or 3 —O— or —S—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,11-diyl, 4,7,10-trioxatridecane-1,13-diyl, 3-thiapentane-1,5-diyl, 4-thiaheptane-1,7-diyl, 3,6-dithiaoctane-1,8-diyl, 4,7-dithiadecane-1,10-diyl, 4,9-dithiadodecane-1,12-diyl, 3,6,9-trithiaundecane-1,11-diyl and 4,7,10-trithiatridecane-1,13-diyl.

An example of $C_5$–$C_7$cycloalkylene is cyclohexylene.

An example of $C_5$–$C_7$cycloalkylenedi($C_1$–$C_4$alkylene) is cyclohexylenedimethylene.

Examples of $C_1$–$C_4$alkylenedi($C_5$–$C_7$cycloalkylene) are methylenedicyclohexylene and isopropylidenedicyclohexylene.

An example of phenylenedi($C_1$–$C_4$alkylene) is phenylenedimethylene.

n is preferably 3 or 4.

$A_8'$, $A_8''$, $A_{10}'$, $A_{10}''$, $A_{12}'$ and $A_{12}''$ are preferably hydrogen or $C_1$–$C_4$alkyl.

Y is preferably —$N(A_6)(A_7)$ or a group of the formula (IV).

$A_2$ and $R_2$ are preferably methylene.

$A_1$ and $R_1$ are preferably independently of one another hydrogen, $C_1$–$C_4$alkyl, —OH, allyl, $C_1$–$C_{12}$alkoxy, $C_5$–$C_8$cycloalkoxy, benzyl, acetyl or acryloyl, in particular hydrogen or $C_1$–$C_4$alkyl such as methyl; or acryloyl.

Preferred compounds of the formula (I) are those wherein $A_3'$ and $A_3''$ are independently of one another $C_1$–$C_{18}$alkyl, $C_2$–$C_{18}$alkyl interrupted by oxygen; or $C_5$–$C_{12}$cycloalkyl;

$A_4$ and $R_4$ are independently of one another $C_1$–$C_{18}$alkyl, $C_2$–$C_{18}$hydroxyalkyl, $C_3$–$C_{18}$alkenyl, $C_5$–$C_{12}$cycloalkyl which is unsubstituted or substituted by 1, 2 or 3 $C_1$–$C_4$alkyl;

$C_7$–$C_{12}$phenylalkyl which is unsubstituted or substituted on the phenyl by 1, 2 or 3 $C_1$–$C_4$alkyl; tetrahydrofurfuryl, a group of the formula (II), or $C_2$–$C_4$alkyl which is substituted in the 2, 3 or 4 position by $C_1$–$C_8$alkoxy, di($C_1$–$C_4$alkyl)amino or a group of the formula (III); and $R_4$ is additionally hydrogen.

Compounds of the formula (I) which are of interest are those wherein $G_1$, $G_2$, $G_3$ and $G_4$ are independently of one another $C_1$–$C_6$alkyl or cyclohexyl or the radicals $G_1$ and $G_2$ and the radicals $G_3$ and $G_4$ form independently of one another, together with the carbon atom they are attached to, cyclohexyl;

$A_2$ is $C_2$–$C_{12}$alkylene or a group —$CA_2'(A_2'')$— with $A_2'$ and $A_2''$ being independently of one another hydrogen, $C_1$–$C_8$alkyl or $C_5$–$C_8$cycloalkyl;

$A_3'$ and $A_3''$ are independently of one another hydrogen, $C_1$–$C_8$alkyl, $C_2$–$C_8$alkyl interrupted by oxygen; or $C_5$–$C_8$cycloalkyl;

$A_4$ is hydrogen, $C_1$–$C_{12}$alkyl, $C_2$–$C_{12}$hydroxyalkyl, $C_3$–$C_{12}$alkenyl, $C_5$–$C_8$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (II) or $C_2$–$C_4$alkyl which is substituted in the 2, 3 or 4 position by $C_1$–$C_4$alkoxy, di($C_1$–$C_4$alkyl)amino or a group of the formula (III);

Y is —$OA_5$, —$N(A_6)(A_7)$ or a group of the formula (IV);

$A_5$, $A_6$ and $A_7$ are independently of one another hydrogen, $C_1$–$C_{12}$alkyl, $C_3$–$C_{12}$alkenyl, $C_5$–$C_8$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by $C_1$–$C_4$alkoxy, di($C_1$–$C_4$alkyl)amino or a group of the formula (III);

or —$N(A_6)(A_7)$ is additionally a group of the formula (III);

when n is 1, Z is —$OA_5$, —$N(A_6)(A_7)$ or a group of the formula (IV);

when n is 2, Z is a group of the formula (V)

wherein $A_8'$ and $A_8''$ are independently of one another hydrogen, $C_1$–$C_{12}$alkyl, $C_3$–$C_{12}$alkenyl, $C_5$–$C_8$cycloalkyl which is unsubstituted or substituted by 1, 2 or 3 $C_1$–$C_4$alkyl;

$C_7$–$C_9$phenylalkyl which is unsubstituted or substituted on the phenyl by 1, 2 or 3 $C_1$–$C_4$alkyl;

tetrahydrofurfuryl, a group of the formula (II) or $C_2$–$C_4$alkyl which is substituted in the 2, 3 or 4 position by —OH, $C_1$–$C_4$alkoxy, di($C_1$–$C_4$alkyl)amino or a group of the formula (III);

$A_9$ is $C_2$–$C_{12}$alkylene, $C_4$–$C_{12}$alkylene interrupted by oxygen; $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi($C_1$–$C_4$alkylene).

Compounds of the formula (I) which are of particular interest are those wherein $G_1$, $G_2$, $G_3$ and $G_4$ are independently of one another $C_1$–$C_4$alkyl;

$A_2$ is $C_2$–$C_{10}$alkylene;

$A_3'$ and $A_3''$ are independently of one another $C_1$–$C_8$alkyl;

$A_4$ is hydrogen, $C_1$–$C_{10}$alkyl, $C_2$–$C_{10}$hydroxyalkyl, $C_3$–$C_{10}$alkenyl, cyclohexyl; benzyl;

tetrahydrofurfuryl, a group of the formula (II) or $C_2$–$C_4$alkyl which is substituted in the 2, 3 or 4 position by methoxy, ethoxy, dimethylamino, diethylamino or a group of the formula (III);

Y is —N($A_6$)($A_7$) or a group of the formula (IV);

$A_6$ and $A_7$ are independently of one another hydrogen, $C_1$–$C_{10}$alkyl, $C_3$–$C_{10}$alkenyl, cyclohexyl; phenyl; benzyl; tetrahydrofurfuryl or $C_2$–$C_4$alkyl which is substituted in the 2, 3 or 4 position by methoxy, ethoxy, dimethylamino, diethylamino or a group of the formula (III);

or —N($A_6$)($A_7$) is additionally a group of the formula (III);

when n is 1, Z is —N($A_6$)($A_7$) or a group of the formula (IV);

when n is 2, Z is a group of the formula (V)

wherein $A_8'$ and $A_8''$ are independently of one another hydrogen, $C_1$–$C_{10}$alkyl, $C_3$–$C_{10}$alkenyl, cyclohexyl, benzyl, tetrahydrofurfuryl, a group of the formula (II) or $C_2$–$C_4$alkyl which is substituted in the 2, 3 or 4 position by —OH, methoxy, ethoxy, dimethylamino, diethylamino or a group of the formula (III);

$A_9$ is $C_2$–$C_{10}$alkylene, $C_4$–$C_{10}$alkylene interrupted by oxygen; cyclohexylene, cyclohexylenedi($C_1$–$C_4$alkylene), $C_1$–$C_4$alkylenedi(cyclohexylene) or phenylenedi($C_1$–$C_4$alkylene).

Especially preferred compounds of the formula (I) are those wherein n is 3 or 4

$G_1$, $G_2$, $G_3$ and $G_4$ are independently of one another $C_1$–$C_4$alkyl;

$A_1$ is hydrogen or $C_1$–$C_4$alkyl;

$A_2$ is $C_2$–$C_{10}$alkylene;

$A_3'$ and $A_3''$ are independently of one another $C_1$–$C_8$alkyl;

$A_4$ is $C_1$–$C_8$alkyl, $C_2$–$C_8$hydroxyalkyl, $C_3$–$C_8$alkenyl, cyclohexyl; benzyl; tetrahydrofurfuryl or a group of the formula (II);

Y is —N($A_6$)($A_7$) or a group of the formula (IV) wherein $R_1$ is hydrogen or $C_1$–$C_4$alkyl, $R_2$ is $C_2$–$C_{10}$alkylene; $R_3'$ and $R_3''$ are independently of one another $C_1$–$C_8$alkyl, and $R_4$ is hydrogen, $C_1$–$C_8$alkyl, $C_2$–$C_8$hydroxyalkyl, $C_3$–$C_8$alkenyl, cyclohexyl, benzyl, tetrahydrofurfuryl or a group of the formula (II);

$A_6$ and $A_7$ are independently of one another hydrogen, $C_1$–$C_8$alkyl, $C_3$–$C_8$alkenyl, cyclohexyl, phenyl, benzyl or tetrahydrofurfuryl;

or —N($A_6$)($A_7$) is additionally a group of the formula (III) with L being —O—;

when n is 3, Z is a group of the formula (VI)

wherein $A_{10}'$ and $A_{10}''$ are independently of one another hydrogen, $C_1$–$C_8$alkyl, $C_3$–$C_8$alkenyl, cyclohexyl, benzyl, tetrahydrofurfuryl or a group of the formula (II), $A_{11}'$ and $A_{11}''$ are independently of one another $C_2$–$C_{10}$alkylene;

when n is 4, Z is a group of the formula (VII)

wherein $A_{12}'$ and $A_{12}''$ have independently of one another one of the definitions of $A_{10}'$ and $A_{10}''$; and $A_{13}'$, $A_{13}''$ and $A_{13}'''$ are independently of one another $C_2$–$C_{10}$alkylene.

A particularly preferred embodiment of this invention relates to compounds of the formula (I) wherein n is 3;

$G_1$, $G_2$, $G_3$ and $G_4$ are independently of one another $C_1$–$C_4$alkyl;

$A_1$ is hydrogen or methyl;

$A_2$ is methylene;

$A_3'$ and $A_3''$ are $C_1$–$C_4$alkyl;

$A_4$ is $C_1$–$C_8$alkyl;

Y is a group of the formula (IV) wherein $R_1$ is hydrogen or methyl, $R_2$ is methylene, $R_3'$ and $R_3''$ are $C_1$–$C_4$alkyl and $R_4$ is hydrogen or $C_1$–$C_8$alkyl; and Z is a group of the formula (VI) with $A_{10}'$ and $A_{10}''$ being independently of one another hydrogen or $C_1$–$C_4$alkyl and $A_{11}'$ and $A_{11}''$ being independently of one another $C_2$–$C_6$alkylene.

Compounds of the formula (I-1) which are preferred are those wherein $G_1$, $G_2$, $G_3$ and $G_4$ are independently of one another $C_1$–$C_4$alkyl;

$A_1$ is methyl;

$A_2$ is a group —$CH_2$—;

$A_3'$ and $A_3''$ are independently of one another $C_1$–$C_4$alkyl; and $A_{13}'$, $A_{13}''$ and $A_{13}'''$ are independently of one another $C_2$–$C_8$alkylene.

Compounds of the formula (I-2) which are preferred are those wherein $G_1$, $G_2$, $G_3$ and $G_4$ are independently of one another $C_1$–$C_4$alkyl;

$A_1$ is hydrogen or methyl;

$A_2$ is a group —$CH_2$—;

$A_4$ is $C_1$–$C_8$alkyl; and $A_{13}'$, $A_{13}''$ and $A_{13}'''$ are independently of one another $C_2$–$C_8$alkylene.

Compounds of the formula (I-3) which are preferred are those wherein $G_1$, $G_2$, $G_3$ and $G_4$ are independently of one another $C_1$–$C_4$alkyl;

$A_1$ is hydrogen or methyl;

$A_2$ is a group —$CH_2$—;

$A_3'$ and $A_3''$ are independently of one another $C_1$–$C_4$alkyl;

Y is —N($C_1$–$C_8$alkyl)$_2$; and $A_{13}'$, $A_{13}''$ and $A_{13}'''$ are independently of one another $C_2$–$C_8$alkylene.

A compound of the formula (I) may be prepared, for example, by reacting a compound of the formula (A-I)

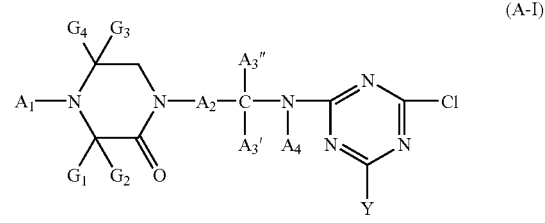

(A-I)

with a compound of the formula (A-II),

H-Z     (A-II)

the radicals $G_1$, $G_2$, $G_3$, $G_4$, $A_1$, $A_2$, $A_3'$, $A_3''$, $A_4$, Y and Z being as defined above, in a stoichiometric ratio or with an excess of up to 10 to 20 molar % of the compound of the formula (A-II).

The reaction is preferably carried out in an inert organic solvent, for example dichloromethane, chloroform, toluene, xylene or benzene, in the presence of a base at a temperature of about 100° to 145° C., in particular 140° C. Preferred bases are NaOH, KOH, $Na_2CO_3$ and $K_2CO_3$.

When Y is a group of the formula (IV), the compound of the formula (A-I) may be prepared, for example, by reacting a compound of the formula (A-III),

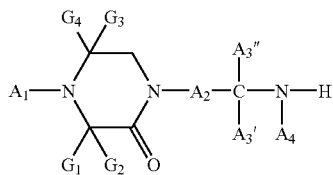 (A-III)

the radicals $G_1$, $G_2$, $G_3$, $G_4$, $A_1$, $A_2$, $A_3'$, $A_3''$ and $A_4$ being as defined above, with cyanuric chloride in a molar ratio of 2.5:1, preferably 2.2:1.

When Y is a group —$N(A_6)(A_7)$, the compound of the formula (A-I) may be prepared, for example, by reacting cyanuric chloride, a compound of the formula (A-III) and a compound of the formula (A-IV),

H—$N(A_6)(A_7)$ (A-IV)

the radicals $A_6$ and $A_7$ being as defined above,
in a molar ratio of 1:1.1:1.1.

The latter two reactions may be carried out at a temperature of −20° to 120° C. in an inert organic solvent, for example one as listed above, in the presence of a base such as NaOH, KOH, $Na_2CO_3$ or $K_2CO_3$.

When Y is —$OA_5$, the compound of the formula (A-I) can be prepared, for example, according to one of the following general procedures.

General Procedure I

A reagent of the formula (R-I)

H—O-$A_5$ (R-I)

with $A_5$ being as defined above is reacted e.g. with a strong base such as sodium alcoholate or lithium amide to obtain a compound of the formula (R-II)

$A_5$-O$^-$M$^+$ (R-II)

with M$^+$ being Na$^+$ or Li$^+$. The reaction is preferably carried out by mixing the reagent (R-I) with the appropriate strong base in an inert organic solvent such as toluene, xylene, benzene or n-hexane. The temperature may be −20° to 120° C., in particular 0° to 15° C.

In a subsequent step, cyanuric chloride, a compound of the formula (A-III) and a compound of the formula (R-II) are reacted in an inert solvent, for example one as listed above, in a ratio of e.g. 1:1.1:1.1. The temperature range is again e.g. −20° to 120° C., in particular 0° to 15° C.

General Procedure II

Cyanuric chloride, a compound of the formula (A-III) and methanol are mixed, for example, in a ratio of 1:1.1:1.1. The reaction may be carried out at a temperature of −20° to 120° C. in an inert solvent, for example toluene, xylene, benzene or n-hexane, in the presence of a base such as NaOH, KOH, $Na_2CO_3$ or $K_2CO_3$. Subsequently, the product obtained is transesterified with a compound of the formula (R-I). The transesterification may be carried out at a temperature of e.g. 0° to 140° C., in particular 50° to 120° C.

When Y is —$SA_5$, the compound of the formula (A-I) may be prepared, for example, by reacting cyanuric chloride, a compound of the formula (A-III) and a compound of the formula (R-III)

H—S-$A_5$ (R-III)

with $A_5$ being as defined above in a molar ratio of 1:1.1:1.1. The reaction may be carried out at a temperature of e.g. −20° to 120° C. in an inert organic solvent, for example toluene, xylene, benzene or n-hexane, in the presence of a base such as NaOH, KOH, $Na_2CO_3$ or $K_2CO_3$.

The compounds of the formula (A-III) may be prepared in analogy to the method shown in EXAMPLES 1A and 3A below.

When Y is —$OA_5$ or —$SA_5$ with $A_5$ being a group of the formula (II), the intermediate of the formula (A-V-1) or (A-V-2)

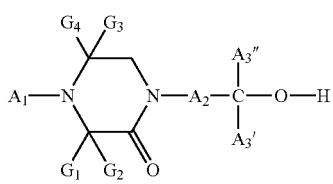 (A-V-1)

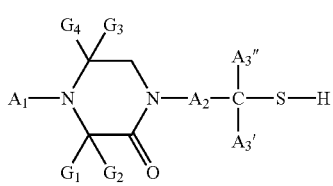 (A-V-2)

may be prepared, for example, in analogy to the procedure disclosed in U.S. Pat. No. 4,167,512 or according to the following reaction scheme.

Scheme

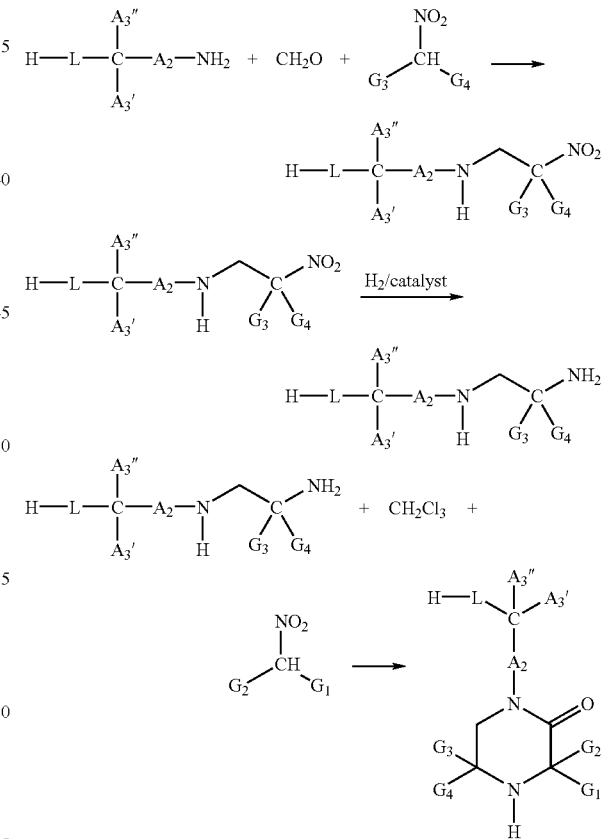

with L being oxygen or sulfur.

A representative example for the preparation of a compound of the formula (A-V-1) or (A-V-2) according to the above scheme is shown below.

Representative Example

Preparation of 1-(2-hydroxyethyl)-3,3,5,5-tetramethylpiperazin-2-one

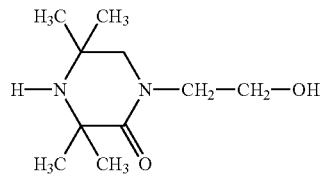

1) Preparation of 2-(2-nitro-2-methyl-propylamino)ethanol 607.8 g (6.55 mol) of 2-nitropropane and 100 ml of water are added to a solution of 450 g (7.40 mol) of ethanolamine in 1000 ml of isopropanol. The solution is stirred at room temperature and 225.4 g (7.5 mol) of paraformaldehyde and 7 ml of 20% aqueous solution of sodium hydroxide (% w/v) are added under stirring and maintaining the temperature at room temperature for 16 hours. The mixture is then heated to 50° C. with nitrogen being bubbled into the mixture to eliminate the formaldehyde in excess. The mixture obtained is used for the following reaction without any isolation of the product.

2) Preparation of 2-(2-amino-2-methyl-propylamino)ethanol

The mixture of 1) is transferred into an autoclave and 100 g of Raney Ni are added. The autoclave is closed and purged with nitrogen. Hydrogen is added until the pressure is 50 bars. The mixture is maintained under a hydrogen pressure of 50 bars at room temperature and under stirring for 8 hours. Subsequently, the mixture is heated to 50° C. at the same pressure. The catalyst is then separated off by filtration and the mixture is distilled under vacuum. A white oil with a boiling point of 100°–105° C. at 13.3 mbar is obtained.

3) 244.2 g (2.05 mol) of chloroform are added to 180 g (1.36 mol) of 2-(2-amino-2-methyl-propylamino)ethanol in 1204 ml of acetone. The mixture is cooled to 5° C. under stirring and a solution of 327 g (8.18 mol) of sodium hydroxide in 327 ml of water is slowly added, the temperature of the mixture being maintained at 0°–5° C. during the addition. The mixture is then stirred at this temperature for further 2 hours and at room temperature for 15 hours. Subsequently, the pH of the aqueous solution is corrected to 11 and the mixture is stirred for further 4 hours. Then, the mixture is filtered and the residue is washed with acetone. The filtrate and the acetone of washing are collected and evaporated under vacuum (70° C./24 mbar). The residue is distilled giving a white oil with a boiling point of 115° C. at 2.66 mbar. After cooling a solid product with a melting point of 91°–93° C. is obtained.

Some of the compounds of the formula (A-III) are novel. Therefore, the compounds of the formula (Z) constitute a further embodiment of this invention.

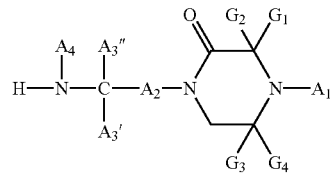

(Z)

wherein $G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

$A_1$ is hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl;

$A_2$ is $C_2$–$C_{14}$alkylene or a group —C$A_2'$($A_2''$)– with $A_2'$ and $A_2''$ being independently of one another hydrogen, $C_1$–$C_{18}$alkyl or $C_5$–$C_{12}$cycloalkyl;

$A_3'$ and $A_3''$ are independently of one another $C_1$–$C_{18}$alkyl, $C_2$–$C_{18}$alkyl interrupted by oxygen; or $C_5$–$C_{12}$cycloalkyl; and $A_3'$ is additionally hydrogen;

$A_4$ is $C_1$–$C_{18}$alkyl, $C_2$–$C_{18}$hydroxyalkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_{12}$phenylalkyl which is unsubstituted or substituted on the phenyl by 1, 2 or 3 $C_1$–$C_4$alkyl; tetrahydrofurfuryl, a group of the formula (II),

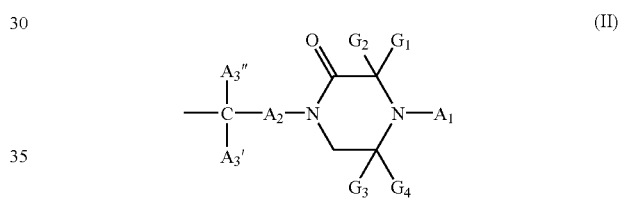

(II)

or $C_2$–$C_4$alkyl which is substituted in the 2, 3 or 4 position by $C_1$–$C_8$alkoxy, di($C_1$–$C_4$alkyl)amino or a group of the formula (III):

(III)

with L being —O—, —CH$_2$—, —CH$_2$CH$_2$— or >N—CH$_3$.

The compounds of the formula (I), (I-1), (I-2) and (I-3) as well as the intermediates of the formula (Z) are very effective in improving the light, heat and oxidation resistance of organic materials, especially synthetic polymers and copolymers.

Examples of organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

This invention thus also relates to a composition comprising an organic material susceptible to degradation induced by light, heat or oxidation and at least one compound of the formula (I), (I-1), (I-2) or (I-3).

The organic material is preferably a synthetic polymer, more particularly one selected from the aforementioned groups.

A thermoplastic rubber (TPR) as an organic material is also of interest.

Polyolefins and their copolymers, for example those listed above under items 1 to 3, in particular polyethylene and polypropylene, are preferred.

This invention further relates to a composition containing a polycarbonate blend or a polyacetal and at least one compound of the formula (I), the proviso being not applied to the definition of the formula (I).

Preferred polycarbonate blends are those listed above under item 28. A polycarbonate/acrylonitrile-butadiene-styrene (PC/ABS) blend is particularly preferred.

Also an embodiment of this invention is a powder coating containing at least one compound of the formula (I), the proviso being not applied to the definition of the formula (I).

Preferred powder coatings are those based on the following resins:

1. Carboxy- or hydroxy-functionalised polyester resins, based on monomers such as terephthalic acid, isophthalic acid, neopentyl glycol, 2-methyl-1,3-propandiol, tris-1,1,1-(hydroxymethyl)propane etc.
2. Epoxy resins based on bisphenols, such as bisphenol A or Novolac® epoxy resins for thermal or uv-cure with cationic photoinitiators.
3. Hydroxy-, carboxy- or glycidyl-functionalised acrylate polymers and copolymers. Suitable comonomers include styrene, alkyl methacrylates, acrylamide, acrylonitrile etc.
4. Unsaturated polyester resins for uv-cureable powder coatings, typically used in conjunction with multifunctional vinyl ethers or acrylate esters.

Powder coatings based on resins with carboxy functionality are typically used together with crosslinking agents of the following classes:

1) polyfunctional epoxy compounds, such as epoxy resins, triglycidylisocyanurate, epoxidised unsaturated fatty acid esters (such as Uranox® resins from DSM), and esters and ethers of glycidol (such as Araldit® PT910 from Ciba Specialty Chemicals).
2) β-hydroxyalkylamides, such as Primid® types XL552 and QM1260 from Ems Chemie.
3) derivatives of melamine, benzoguanimine and glycoluril, such as Powderlink® 1174 from American Cyanamid.

Crosslinking agents for resins of hydroxy functionality include anhydrides and especially blocked diisocyanates and uretdiones, etc.

Powder coatings based on resins with epoxy functionality are typically used together with crosslinking agents such as diacids (such as 1,12-dodecanedioic acid), carboxy-functional polyesters, carboxy-functional copolymers of acrylates and methacrylates, anhydrides (such as the anhydride prepared from 1,12-dodecanedioic acid).

Other additives that can be used together with the compounds of this invention in powder coatings include: degassing agents, flow promoters, tribocharging additives cure catalysts, sensitisers, cationic and free-radical photoinitiators, as well as typical liquid paint additives.

The compounds according to this invention are particularly useful in formulations of high reactivity, such as the glycidylmethacrylate-functionalised acrylics. Here, the combination of the compounds of this invention together with UV-absorbers, especially of the hydroxyphenyltriazine class, can be used to improve the weatherability without causing catalysis. In other binder systems and with other classes of UV-absorbers, such as those previously mentioned to be of particular use in automotive paints, synergistic effects on the weatherability are also found.

In powder coatings the compounds of this invention can also be used to improve the oxidative stability and reduce yellowing on curing and overbaking. Here not only is the low basicity advantageous, but also the ability to withstand and prevent yellowing caused by oxides of nitrogen in gas-fired ovens. Use together particularly with phosphite and phosphonite costabilizers, as disclosed in EP-A-816,442, and dialkylesters of dithiopropionic acid is particularly beneficial. The compounds of this invention can, where appropriate also be used to stabilize polyesters during manufacture as well as at all stages of its subsequent use.

A further embodiment of this invention is a recording material, in particular a photographic material, containing at least one compound of the formula (I), the proviso being not applied to the definition of the formula (I).

Recording materials for photographic reproduction and other reprographic techniques are described for example in Research Disclosure 1990, 31429 (pages 474–480), GB-A-2,319,523 or DE-A-19,750,906, page 22, line 15 to page 105, line 32.

Of special importance is also the stabilization of non-silver reprographic materials, for example, those used for pressure-sensitive copying systems, microcapsule photocopier systems, heat-sensitive copier systems and ink-jet printing.

The recording materials stabilized with the compounds of the formula (I) have an unexpectedly high quality, especially in terms of their light stability.

The recording materials have a structure which is known per se and which corresponds to their utility. They consist of a base, for example a paper or plastic film, on which one or more coatings are applied. Depending on the type of the material, these coats contain the suitable components required. In the case of photographic materials, the coats contain for example silver halide emulsions, colour couplers, dyes and the like. The material intended for ink-jet printing has e.g. a customary base on which an absorption layer suitable for ink is located. Uncoated paper can likewise be employed for ink-jet printing. In the latter case, the paper simultaneously functions as a base and has the absorbent for the ink. Suitable materials for ink-jet printing are described, inter alia, in U.S. Pat. No. 5,073,448, the disclosure content of which is regarded as part of the present description.

The recording material can also be transparent, for example in the case of projection films.

The compound of the formula (I) can be incorporated into the material even in the course of manufacture; in papermaking, for example, by addition to the pulp. Another method of use is the spraying of the material with an aqueous solution of the compound of the formula (I), or the addition thereof to the coating.

Coatings for transparent recording materials for projection must not contain any light-scattering particles such as pigments or fillers.

The colour-binding coatings can contain further additives, for example antioxidants, light stabilizers (including UV absorbers and/or conventional hindered amine light stabilizers), viscosity improvers, brighteners, biocides and/or antistats.

The coating is usually prepared as described in the following. The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula (I) is that they can easily be incorporated into the coating.

As mentioned above, the recording materials cover a broad field of use. Compounds of the formula (I) can be employed, for example, in pressure-sensitive copier systems. They can be added to the paper to protect the microencapsulated dye precursors against light, or to the binder of the developer layer for protecting the dyes formed therein.

Photocopier systems with light-sensitive microcapsules which are developed by pressure are described, inter alia, in U.S. Pat. No. 4,416,966, U.S. Pat. No. 4,483,912, U.S. Pat. No. 4,352,200, U.S. Pat. No. 4,535,050, U.S. Pat. No. 4,536,463, U.S. Pat. No. 4,551,407, U.S. Pat. No. 4,562,137 and U.S. Pat. No. 4,608,330 and also in EP-A-139,479, EP-A-162,664, EP-A-164,931, EP-A-237,024, EP-A-237,025 and EP-A-260,129. In all these systems, the compounds of the formula (I) can be added to the colour-accepting layer. Alternatively, the compounds of the formula (I) can be added to the donor layer for protecting the colour formers against light.

The compounds of the formula (I) can also be employed in recording materials which are based on the principle of photopolymerization, photosoftening or the rupture of microcapsules, or, when heat-sensitive or photosensitive diazonium salts, leuco dyes with oxidizing agent or colour lactones with Lewis acids are used.

Heat-sensitive recording material exploits the colour-imparting reaction between a colourless or weakly coloured base dye and an organic or inorganic colour developer; the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula (I). If a protective layer is present, the compound of the formula (I) can also be incorporated into the protective layer.

Heat-sensitive recording materials are described, for example, in JP-A-Hei 8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing as described for example in EP-A-507,734.

Compounds of the formula (I) can also be employed in inks (preferably for ink-jet printing) for example as described in U.S. Pat. No. 5,098,477, the disclosure content of which is regarded as part of the present description. The invention therefore preferably also relates to an ink comprising at least one compound of the formula (I) as stabilizer. The ink, especially for ink-jet printing, contains preferably water. Inks contain the stabilizer of the formula (I) usually in a concentration of from 0.01 to 20% by weight, in particular from 0.5 to 10% by weight.

The photographic material according to this invention can be a black and white or can be a colour photographic material. A colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process.

Details of the photographic materials to be stabilized according to this invention and components which can be employed therein are given, inter alia, in GB-A-2,319,523, DE-A-19,750,906, page 23, line 20 to page 105, line 32, and U.S. Pat. No. 5,538,840, column 25, line 60 to column 106, line 31. These parts of U.S. Pat. No. 5,538,840 are incorporated herein by way of reference.

The compounds of this invention can be introduced in any layer of a silver halide photographic material, however, they are preferably incorporated in a chromogenic layer, in particular in a layer containing a yellow coupler. They are used, for example, in a 1% to 200% weight ratio with the coupler, preferably 1% to 100%. The compounds of the present invention can be used in combination with other conventional stabilizers that can be incorporated in the same layer or in a different layer. Examples of suitable conventional stabilizers are described in GB-A-2,319,523, DE-A-19,750, 906 and U.S. Pat. No. 5,538,840 and include in particular phenolic stabilizers, conventional hindered amine stabilzers, UV absorbers, preferably those of the hydroxyphenyl benztriazole type or of the hydroxyphenyl triazine class, and the like.

Examples of yellow couplers are also disclosed in U.S. Pat. No. 5,538,840, column 33, line 3 to column 47, line 15.

Thus, further preferred embodiments of this invention are:

(1) A photographic material comprising on a substrate at least one layer containing a compound of the formula (I).

(2) A silver halide colour photographic material comprising a support having thereon at least one light-sensitive silver halide emulsion layer and optionally a non-light sensitive emulsion layer, characterized in that at least one light-sensitive layer contains a compound of the formula (I).

(3) A silver halide colour photographic material comprising a support having thereon a) at least one cyan-forming unit composed of a red-sensitive silver halide emulsion layer containing a cyan dye-forming coupler, b) at least one magenta-forming unit composed of a green-sensitive silver halide emulsion layer containing a magenta dye-forming coupler and c) at least one yellow-forming unit composed of a blue-sensitive silver halide emulsion layer containing a yellow dye-forming coupler, characterized in that
the blue-sensitive layer contains a compound of the formula (I).

A further embodiment of this invention is a recording material containing at least one compound of the formula (P-1)

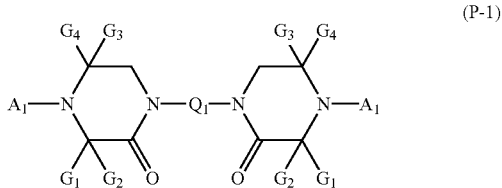

wherein $G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

the radicals $A_1$ independently of one another are hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl; and $Q_1$ is $C_1$–$C_{20}$alkylene, $C_4$–$C_{20}$alkenylene, $C_4$–$C_{20}$alkynylene or a group of the formula -Q$_2$-R-Q$_2$-(R-Q$_2$)$_v$- with v being zero or 1, the radicals $Q_2$ being independently of one another a direct bond or $C_1$–$C_{10}$alkylene, the radicals R being independently of one another a saturated or unsaturated monocyclic hydrocarbon ring with two free valences, 5 to 7 carbon atoms and optionally substituted by $C_1$–$C_4$alkyl; or a saturated or unsaturated bicyclic hydrocarbon ring with two free valences, 8 to 10 carbon atoms and optionally substituted by $C_1$–$C_4$alkyl.

A particularly preferred recording material corresponds to a silver halide colour photographic material comprising a support having thereon at least one light-sensitive silver halide emulsion layer and optionally a non-light sensitive emulsion layer, characterized in that at least one light-sensitive layer contains a compound of the formula (P-1).

The disclosure given above for a recording material containing a compound of the formula (I) also applies to a recording material containing a compound of the formula (P-1). Further, the explanations and preferred embodiments given above for the radicals $G_1$, $G_2$, $G_3$, $G_4$ and $A_1$ for the formula (I) also apply to the formula (P-1).

Examples of alkylene containing up to 20 carbon atoms are methylene, ethylene, propylene, trimethylene, tetramethylene, pentamethylene, hexamethylene, octamethylene, decamethylene, dodecamethylene, tridecamethylene, tetradecamethylene, pentadecamethylene and octadecamethylene. $C_8$–$C_{20}$alkylene is preferred, in particular $C_{10}$–$C_{14}$alkylene.

Examples of $Q_1$ as $C_4$–$C_{20}$alkenylene are 2-but-1,4-enylene, 3-pent-1,5-enylene or 2-hex-1,6-enylene.

Examples of $Q_1$ as $C_4$–$C_{20}$alkynylene are 2-butynylene (—CH$_2$—C≡C—CH$_2$—), 2-pentynylene, 2-hexynylene, 3-hexynylene, 3-heptynylene, 2-decynylene, 4-decynylene or 8-octadecynylene.

Illustrative examples of a saturated or unsaturated monocyclic hydrocarbon ring with two free valences, 5 to 7 carbon atoms and optionally substituted by $C_1$–$C_4$alkyl are $C_5$–$C_7$cycloalkylene unsubstituted or substituted by methyl, in particular cyclopentylene, cyclohexylene, methylcyclohexylene or cycloheptylene; or phenylene. Cyclohexylene and phenylene are preferred.

Illustrative examples of a saturated or unsaturated bicyclic hydrocarbon ring with two free valences, 8 to 10 carbon atoms and optionally substituted by $C_1$–$C_4$alkyl are

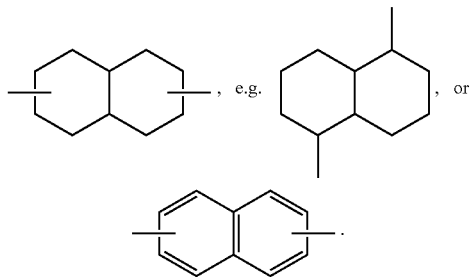

Particularly preferred examples of the radicals $Q_1$ are

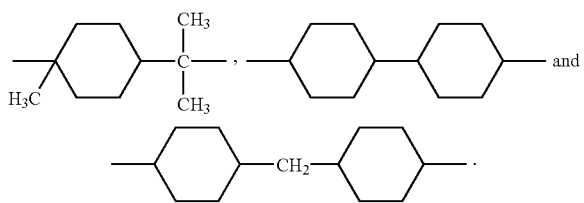

Some compounds of the formula (P-1) are novel. Therefore, the present invention also relates to a compound of the formula (P-2)

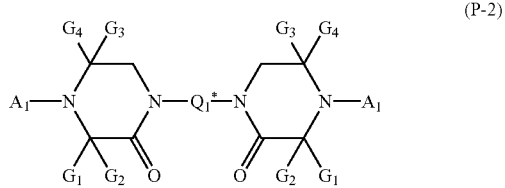

(P-2)

wherein $G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

the radicals $A_1$ independently of one another are hydrogen, $C_1$–$C_{18}$alkyl, oxyl, —OH, —$CH_2CN$, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —$CH_2CH(OH)(G)$ with G being hydrogen, methyl or phenyl; and $Q_1^*$ is $C_8$–$C_{20}$alkylene, $C_4$–$C_{20}$alkenylene, $C_4$–$C_{20}$alkynylene or a group of the formula

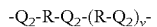

with v being zero or 1, the radicals $Q_2$ being independently of one another a direct bond or $C_1$–$C_{10}$alkylene, the radicals R being independently of one another a saturated or unsaturated monocyclic hydrocarbon ring with two free valences, 5 to 7 carbon atoms and optionally substituted by $C_1$–$C_4$alkyl; or a saturated or unsaturated bicyclic hydrocarbon ring with two free valences, 8 to 10 carbon atoms and optionally substituted by $C_1$–$C_4$alkyl, with the proviso that $Q_1^*$ is different from cyclohexylene, phenylene and methylene-phenylene-methylene.

A compound of the formula

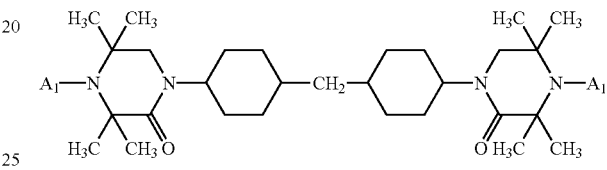

wherein $A_1$ is hydrogen, methyl or acryloyl, is particularly preferred.

The compounds of the formula (P-2) are useful in the same applications as the compounds of the formula (I).

A representative method for the preparation of the compounds of the formula (P-2) is described in EXAMPLES 10 to 14.

A particularly preferred embodiment of this invention is a composition being in contact with a pesticide, said composition containing a polyolefin or a polyolefin copolymer and at least one compound of the formula (I) according to claim 1, the proviso being not applied to the definition of the formula (I).

Polyolefin or polyolefin copolymer films which are employed in agricultural, especially in greenhouse applications are of interest.

The pesticides which may contribute to a faster photodegradation, often are those containing halogen and/or sulfur atoms. Halogen containing pesticides usually embrace compounds containing fluorine, chlorine or bromine, especially chlorine. Compound classes, whose detrimental effects on the photostability of polyolefin or polyolefin copolymer films can be most effectively prevented by the compounds of this invention (in particular the compounds of formula (I-3) such as the compound of Example 8 as shown below) include pyrethroides of the permethrin and fenvalerate type, thioureas, dithiocarbamates, thio- and isothiocyanates and compounds generating these compounds, especially permethrin type compounds containing chlorine and dithiocarbamates such as derivatives of vinylidene dichloride and metal salts of alkyldithiocarbamic acid.

A further embodiment of this invention is a method for stabilizing an organic material, in general, against degradation induced by light, heat or oxidation, which comprises incorporating into said organic material at least one compound of the formula (I), (I-1), (I-2) or (I-3).

A preferred object of this invention is a method for stabilizing a polyolefin or a polyolefin copolymer greenhouse film against the detrimental effects of pesticides and light, heat or oxidation, which comprises incorporating into the polyolefin or polyolefin copolymer film at least one compound of the formula (I), the proviso being not applied to the definition of the formula (I).

The compounds of the formula (I), (I-1), (I-2) or (I-3) can be used in various proportions depending on the nature of the material to be stabilized, on the end use and on the presence of other additives.

In general, it is appropriate to use, for example, 0.01 to 5% by weight of the compounds according to this invention, relative to the weight of the material to be stabilized, preferably 0.05 to 2%, in particular 0.05 to 1%.

The compounds of this invention can be added, for example, to the polymeric materials before, during or after the polymerization or crosslinking of the said materials. Furthermore, they can be incorporated in the polymeric materials in the pure form or encapsulated in waxes, oils or polymers.

In general, the compounds of this invention can be incorporated in the polymeric materials by various processes, such as dry mixing in the form of powder, or wet mixing in the form of solutions or suspensions or also in the form of a masterbatch which contains the compounds of this invention in a concentration of 2.5 to 25% by weight; in such operations, the polymer can be used in the form of powder, granules, solutions, suspensions or in the form of latices.

The materials stabilized with the compounds of this invention can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, corrosion inhibitors and metal deactivators, can be added to the organic materials containing the compounds of this invention.

Particular examples of said conventional additives are:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-di-methyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxvbenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl)phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tertbutylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino) ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol di-phosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tertbutyl-1,1'-biphenyl-2,2'-diyl)phosphite], 2-ethyl hexyl(3,3',5,5'-tetra-tert-butyl-1,1'-biphenyl-2,2'-diyl)phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecylalpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-di-methylphenyl)-5,7-di-tert-butyl-benzofuran-2-one.

The weight ratio of the compounds of this invention to the conventional additives may be for example 1:0.5 to 1:5.

This invention is illustrated in more detail by the following examples. All percentages are by weight, unless otherwise indicated.

Preferred compounds of the formula (I) are shown in the following EXAMPLES 1 to 4.

EXAMPLE 1

A) Preparation of the Intermediate of the Formula

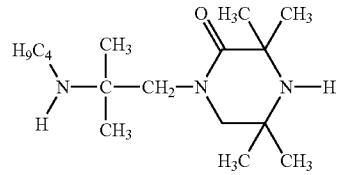

To a solution of 65 g (0.286 mol) of 1-(2-amino-2-methylpropyl)-3,3,5,5-tetramethyl-piperazin-2-one (product of EXAMPLE 3A below) in 130 ml of tert-amyl alcohol, 47 g (0.34 mol) of 1-bromobutane are added and the solution is stirred at 85° C. for 5 hours. The mixture is cooled to room temperature and 34.7 g (0.344 mol) of triethylamine are added. The mixture is heated to 85° C. and allowed to react for additional 4 hours.

Then, the reaction mixture is cooled to room temperature, diluted with 260 ml of dichloromethane and washed three times with 100 ml of water. The organic layer is separated, dehydrated under sodium sulfate and concentrated under vacuum. A colourless liquid is recovered.

$^1$H NMR: 3.19 (s, 2H); 3.18 (s, 2H); 2.37 (t, 2H); 1.74 (m, 10H); 0.98 (s, 6H); 0.89 (s, 6H); 0.73 (t, 3H).

B) Preparation of the Intermediate of the Formula

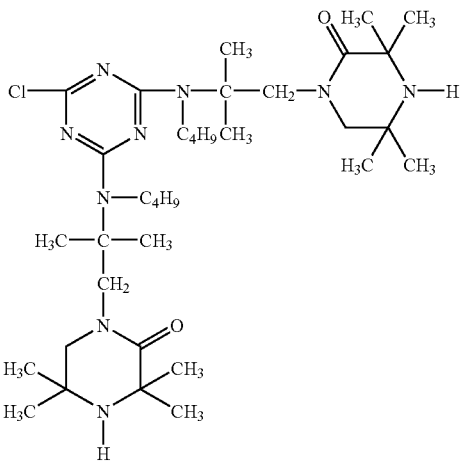

To a solution of 24 g (0.13 mol) of cyanuric chloride in 240 ml of xylene, 83 g (0.292 mol) of 1-(2-butylamino-2-methylpropyl)-3,3,5,5-tetramethylpiperazin-2-one are added. The solution is heated to 145° C. and allowed to react for 90 min. Then, it is cooled to 60° C. and 5.2 g (0.13 mol) of NaOH in 10 ml of water are slowly added. The mixture is stirred for additional 20 min and subsequently, the temperature is increased in order to distill off the water. The mixture is allowed to react at 140° C. for additional 4 hours. Then, the mixture is cooled and 36 g of potassium carbonate in 25 ml of water are added. The water is again distilled off and the mixture is allowed to react for additional 16 hours.

Then, the mixture is cooled to room temperature, diluted with 40 ml of toluene and washed twice with an acidic water solution as well as twice with 100 ml of water. The organic layer is separated, dehydrated under sodium sulfate and concentrated under vacuum.

C) Preparation of the Compound of the Formula

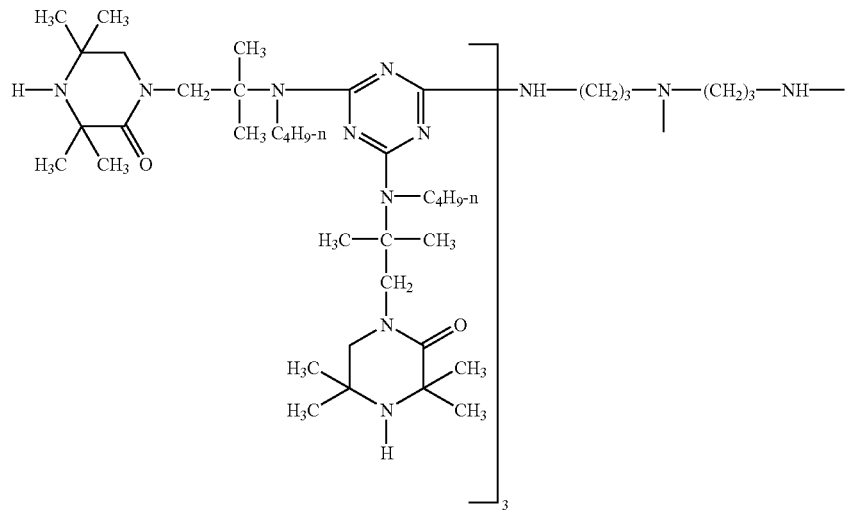

To a solution of 4.15 g (0.0316 mol) of 1-(3-aminopropyl) propane-1,3-diamine in 150 ml of xylene, 66 g (0.0974 mol) of the intermediate described under B) are added. The solution is heated to reflux for three hours. Then, the solution is cooled to 60° C. and 2 g (0.05 mol) of NaOH in 15 ml of water are added. The mixture is heated in order to distill off the water and allowed to reflux for additional 16 hours. Subsequently, the mixture is cooled, diluted with 50 ml of toluene and washed three times with water. The organic layer is separated, dehydrated under sodium sulfate and concentrated under vacuum. A pale yellow solid is recovered.

Melting point: 89°–95° C.

EXAMPLE 2

Preparation of the Compound of the Formula

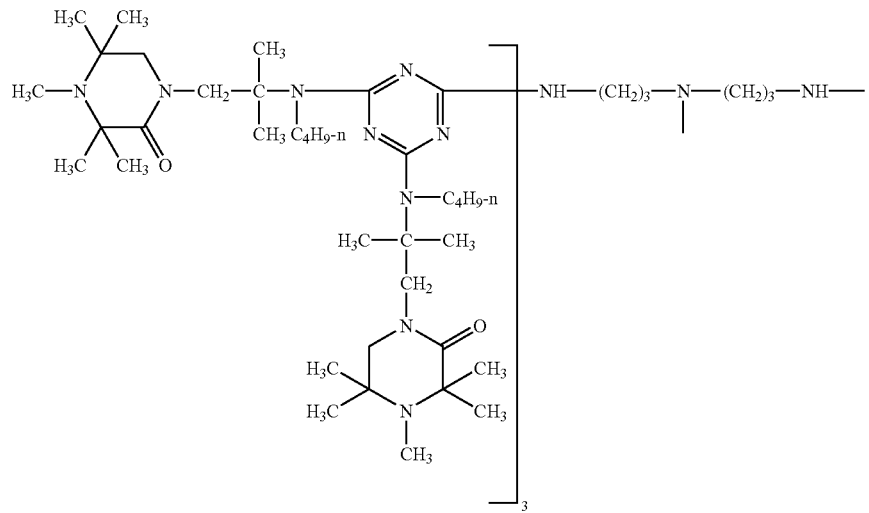

To a solution of 37.1 g (0.0131 mol) of the compound of EXAMPLE 1C dissolved in 140 ml of water, 7.6 g (0.243 mol) of paraformaldehyde and 9.2 g (0.200 mol) of formic acid are added. The solution is heated under reflux for 16 hours. After cooling to room temperature, 150 ml of xylene are added and then, 8.8 g of sodium hydroxide in 50 ml of water are added. After stirring for 2 hours, the organic layer is separated, washed with water and dried over sodium sulfate. After filtration, the organic phase is evaporated under vacuum. A pale yellow solid is obtained after drying.

Melting point: 104–107° C.

EXAMPLE 3

A) Preparation of the Intermediate of the Formula

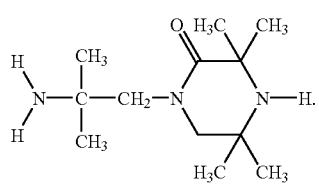

1) Preparation of bis-(2-methyl-2-nitropropyl)amine

A solution of 800 g (6.716 mol) of 2-methyl-2-nitropropanole in 1500 ml of methanol and 435 g of a solution of ammonia in methanol (12% w/w) and 433.6 g (3.053 mol) of anhydrous sodium sulphate are added into an autoclave. The mixture is heated to 80° C. and allowed to react for 90 hours. The reaction mixture is cooled to room temperature and evaporated under vacuum. The residue is dissolved in 1500 ml of toluene and washed three times with 300 ml of water. The organic solution is dehydrated under sodium sulphate and concentrated at 80° C.

2) Preparation of bis-(2-methyl-2-amino-propyl)amine 490 g (2.23 mol) of bis-(2-methyl-2-nitropropyl)amine from reaction 1) are dissolved in 1200 ml of methanol and transferred into an autoclave. 60 g of Raney Ni are added. The autoclave is closed and purged with nitrogen. Then, hydrogen is added until the hydrogen pressure is 50 bars. That pressure is maintained at room temperature for 8 hours and, subsequently, the reaction mixture is heated to 50° C. at the same pressure. The catalyst is then separated off by filtration and the mixture is distilled under vacuum (100° C./33.3 mbar). A colourless oil is recovered (Boiling point: 110° C./5 mbar).

3) 184 g (1.54 mol) of chloroform are added to 163.5 g (1.027 mol) of bis-(2-methyl-2-aminopropyl)amine from reaction 2) in 895 g (15.4 mol) of acetone. The mixture is cooled to 5° C. under stirring and a solution of 246.6 g (6.16 mol) of NaOH in 246 ml of water is slowly added, the temperature of the mixture being maintained at 0 to 5° C. during the addition. The mixture is then stirred at this temperature for further 2 hours and at room temperature for additional 15 hours. The mixture is filtered and the residue is washed with acetone. The filtrate and the acetone of washing are collected and evaporated under vacuum (70° C./24 mbar). The row material is purified by distillation under vacuum. A colourless oil is obtained.

$^1$HNMR: 3.62 (s, 2H); 3.08 (s, 2H); 1.16 (broad s, 2H); 1.09 (s, 6H); 0.90 (s, 6H); 0.86 (s, 6H)

B) Preparation of the Intermediate of the Formula

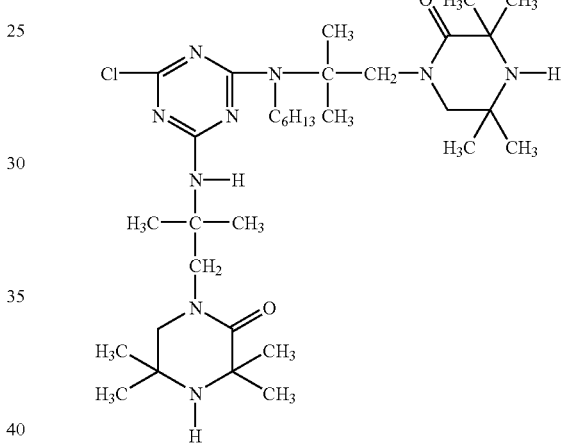

Following the procedure described in EXAMPLE 1A, under the same experimental conditions and using the appropriate reagent, 1-(2-hexylamino-2,2-dimethylethyl)-3,3,5,5-tetramethyl-piperazin-2-one is prepared.

To a solution of 23.7 g (0.129 mol) of cyanuric chloride in 240 ml of toluene, 40 g (0.129 mol) of 1-(2-hexylamino-2,2-dimethylethyl)-3,3,5,5-tetramethylpiperazin-2-one in 40 ml of toluene are slowly added drop by drop at 20°–25° C. The solution is stirred for 1 hour and 21.2 g (0.154 mol) of anhydrous potassium carbonate are added. The mixture is left to react overnight at room temperature and then, 35 g (0.154 mol) of 1-(2-amino-2-methylpropyl)-3,3,5,5-tetramethylpiperazin-2-one (the intermediate described under A) and 213 g (0.154 mol) of anhydrous potassium carbonate are added. The temperature is increased to 95° C. and the mixture is allowed to react for additional 8 hours. After cooling to room temperature, 150 ml of water are added. The organic layer is separated, dried under sodium sulfate and evaporated under vacuum.

C) Preparation of the Compound of the Formula

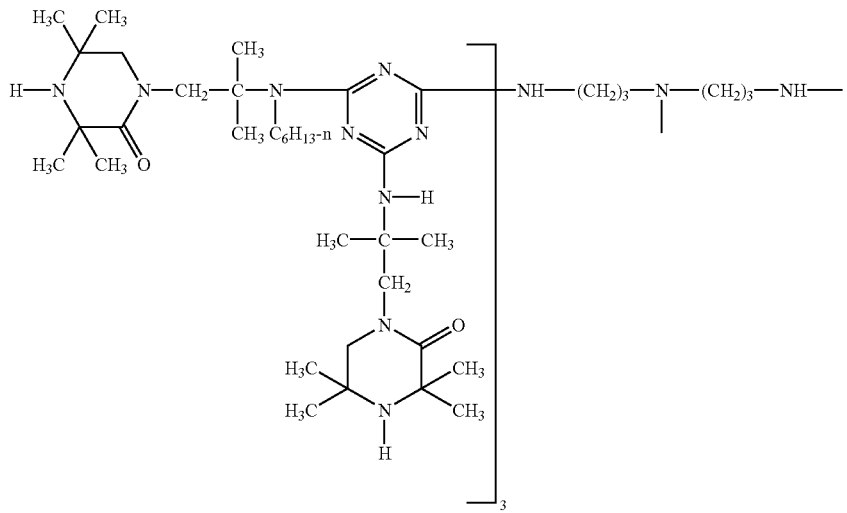

The compound is prepared following the procedure described in EXAMPLE 1C), under the same experimental conditions and using the appropriate reagents. A pale yellow powder is obtained.

Melting point: 91°–95° C.

EXAMPLE 4

Preparation of the Compound of the Formula

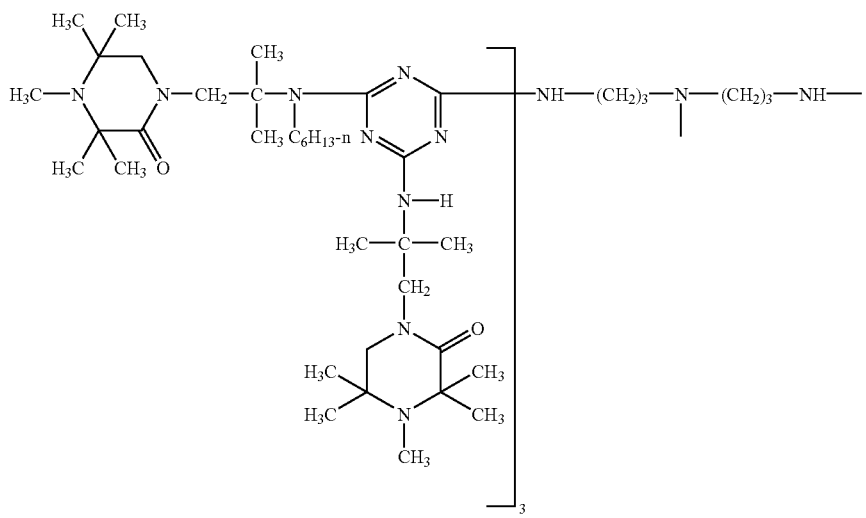

The compound is prepared following the procedure described in EXAMPLE 2, under the same experimental conditions and using the appropriate reagents. A powder is obtained.

Melting point: 98°–102° C.

EXAMPLE 5

Preparation of the Compound of the Formula

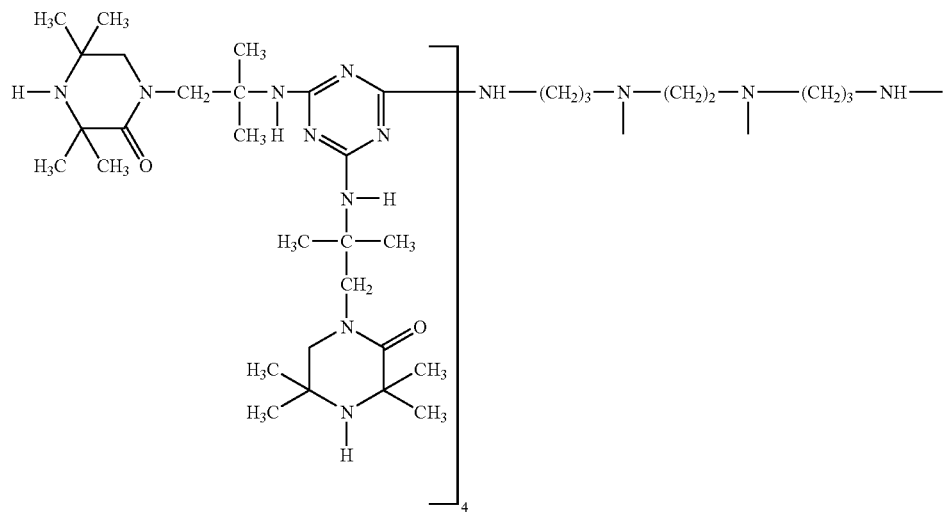

The compound is prepared following the procedure described in EXAMPLE 1C, under the same experimental conditions and using the appropriate reagents. A yellow powder is obtained Melting point: 126°–133° C.

A preferred compound of the formula (I-1) is shown in the following EXAMPLE 6.

EXAMPLE 6

Preparation of the Compound of the Formula

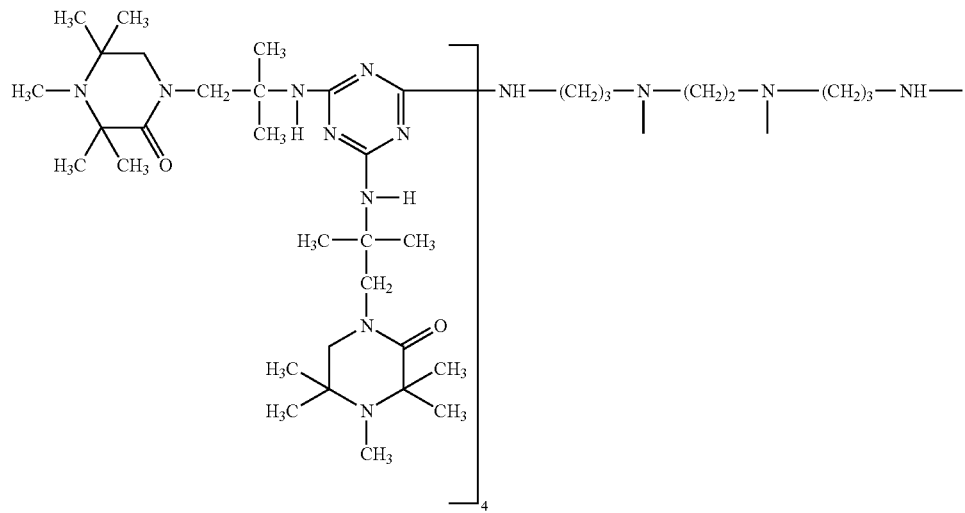

The compound is prepared following the procedure described in EXAMPLE 2, under the same experimental conditions and using the appropriate reagents.

Melting point: 136°–139° C.

A preferred compound of the formula (I-2) is shown in the following EXAMPLE 7.

EXAMPLE 7

Preparation of the Compound of the Formula

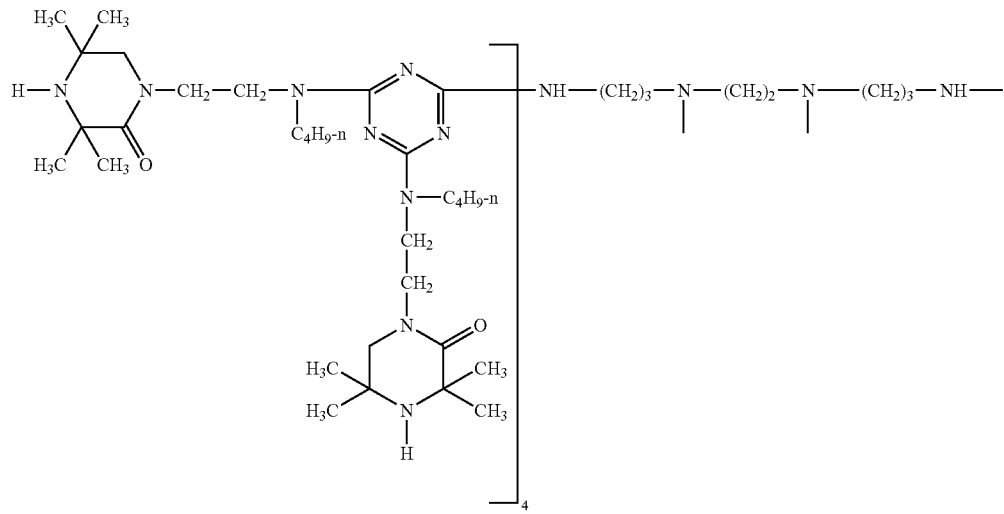

The compound is prepared following the procedure described in EXAMPLE 1C, under the same experimental conditions and using the appropriate reagents. A yellow powder is obtained.

Melting point: 68°–70° C.

Preferred compounds of the formula (I-3) are shown in the following EXAMPLES 8 and 9.

EXAMPLE 8

A) Preparation of the Intermediate of the Formula

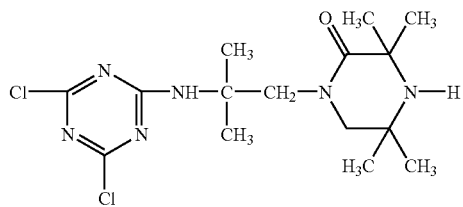

A solution of 57 g (0.309 mol) of cyanuric chloride dissolved in 570 ml of dichloromethane is cooled to 5° C. and 70 g (0.308 mol) of the intermediate described in EXAMPLE 3A, dissolved in 70 ml of dichloromethane are added drop by drop. The mixture is left to react for 30 minutes at 5° C. Then, 10 g (0.25 mol) of NaOH in 10 ml of water are slowly added. The temperature is increased to room temperature and the reaction is left to react for 30 minutes. Subsequently, 80 ml of water are added. The organic layer is separated and washed twice with water. Then, the organic layer is dehydrated under sodium sulfate and evaporated under vacuum. The row material is recrystallized from xylene.

B) Preparation of the Compound of the Formula

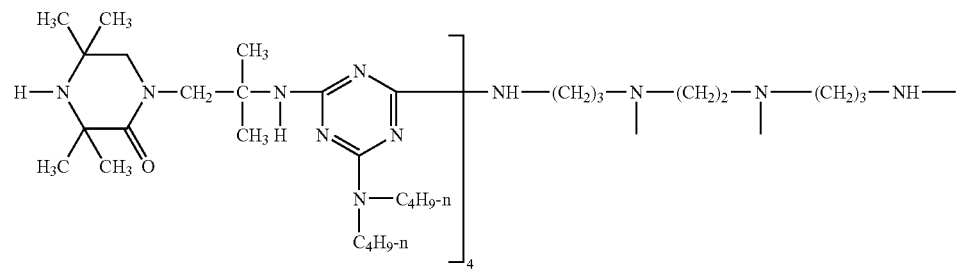

9.5 g (0.0545 mol) of N,N'-bis(3-aminopropyl)ethylenediamine in 50 ml of dichloromethane are added to a solution of 80 g (0.215 mol) of the product obtained according to A), in 100 ml of dichloromethane cooled to 0° C. After the addition, the reaction is left to react for 30 minutes at 0° to 5° C. Then, 10 g (0.25 mol) of NaOH in 10 ml of water are slowly added. After the addition, the temperature is increased to 40° C. and the mixture is left to react for additional 2 hours. Dichloromethane is distilled off and is replaced by 200 ml of xylene. 32 g (0.248 mol) of dibutylamine is then added at 100° C. The mixture is cooled to 80° C. and 40 g of $K_2CO_3$ in 60 ml of water are added. The water is then distilled off and the reaction mixture is left to react at 138° C. for 9 hours. The mixture is cooled to 60° C. and 200 ml of water are added. The organic layer is separated and washed twice with 100 ml of water, dehydrated with sodium sulfate and evaporated under vacuum. The product obtained has a melting point of 72° to 74° C.

| Elemental Analysis: | | | |
|---|---|---|---|
| Calculated: | C = 63.1% | H = 9.8% | N = 23.5% |
| Found: | C = 63.3% | H = 9.8% | N = 23.3% |

EXAMPLE 9

Preparation of the Compound of the Formula

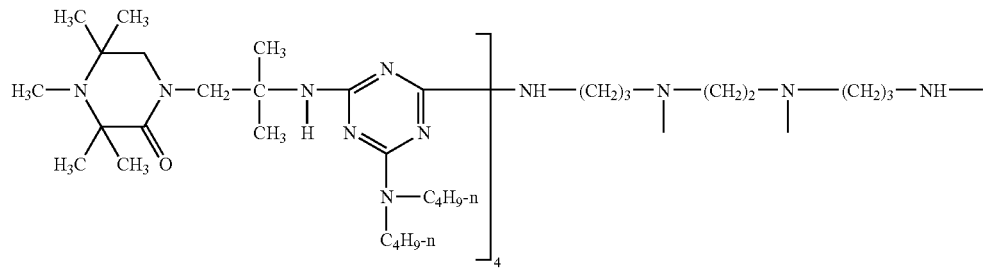

16 g (0.512 mol) of paraformaldehyde are added to a solution of 21 g (0.0111 mol) of the compound of EXAMPLE 8B in 150 ml of tert-amyl alcohol. The mixture is heated to 80° C. and 24.4 g (0.540 mol) of formic acid in 10 ml of tert-amyl alcohol are slowly added. Then, the mixture is stirred for 3 hours at 80° C. 300 ml of toluene are added and, subsequently, the mixture is cooled to room temperature. A solution of 23 g (0.575 mol) of sodium hydroxide in 100 ml of water is added. After stirring for 1 hour, the organic phase is separated, is washed with water, dried over anhydrous sodium sulfate, and evaporated under vacuum (80° C./1.3 mbar). A pale yellow powder with a melting point of 72° to 75° C. is recovered.

| Elemental Analysis: | | | |
|---|---|---|---|
| Calculated: | C = 63.8% | H = 9.9% | N = 22.9% |
| Found: | C = 63.6% | H = 9.8% | N = 22.4% |

Preferred compounds of the formulae (P-1) and (P-2) are shown in the following EXAMPLES 10 to 14.

EXAMPLE 10

Preparation of the Compound of the Formula

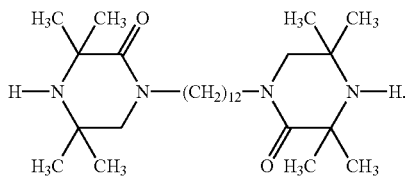

A) Preparation of N,N'-bis(2-methyl-2-nitro-propyl)dodecane-1,12-diamine 48.6 g (0.54 mol) of 2-nitropropane are added to a solution of 50 g (0.25 mol) of dodecanediamine in 200 ml of isopropanol and 30 ml of water. The solution is stirred at room temperature and 17.2 g (0.55 mol) of paraformaldehyde and 0.8 ml of a 20% aqueous solution of sodium hydroxide (% W/V) are added, under stirring and maintaining the temperature at room temperature for 16 hours. To this mixture, 300 ml of methylene chloride and 100 ml of water are added. Then, the organic layer is separated off, dried under sodium sulfate and evaporated in vacuum.

B) Preparation of N,N'-bis(2-amino-2-methyl-propyl)dodecane-1,12-diamine.

40 g of the product from reaction A) are dissolved in 1000 ml of methanol and 30 g of Raney nickel are added. The mixture is transferred into an autoclave which is closed and purged with nitrogen. Then, hydrogen is added until a pressure of 50 bars. The mixture is maintained under a hydrogen pressure of 50 bars, at room temperature and under stirring for 8 hours. Subsequently, the mixture is heated to 50° C. at the same pressure. Then, the catalyst is separated off by filtration. The mixture is evaporated under vacuum and crystallized from n-octane.

C) 51 g (0.15 mol) of the product from reaction B) are suspended in 250 ml of toluene and 30 ml of water. 50 g (1.25 mol) of NaOH are added and the mixture is stirred until complete dissolution and cooled to 5° C. 40 g (0.67 mol) of acetone and 7 g (0.03 mol) of benzyl triethyl ammonium chloride are added. To the mixture cooled at 5° C., 45 g (0.38 mol) of $CHCl_3$ are slowly added during 3 hours. After this addition, the temperature is allowed to reach room temperature. The mixture is filtered off and the organic phase is washed twice with 20 ml of water. Then, the row material is crystallized from n-octane.

| Elemental analysis: | | | |
|---|---|---|---|
| Calculated: | C = 71.0 | H = 11.5 | N = 11.1 |
| Measured: | C = 70.5 | H = 11.4 | N = 11.1 |

EXAMPLE 11

Preparation of the Compound of the Formula

[Chemical structure: a bis-piperidinone compound with H—N and N—H termini connected via —(CH$_2$)$_{12}$— linker, each piperidinone ring bearing gem-dimethyl groups and a carbonyl]

2.9 g (0.09 mol) of paraformaldehyde are added to a solution of 16 g (0.03 mol) of the compound of EXAMPLE 10 in 50 ml of tert-amyl alcohol. The mixture is heated to 80° C. and 0.08 mol of formic acid dissolved in tert-amyl alcohol are slowly added. The mixture is allowed to react for further 1 hour and is then cooled to 50° C. 200 ml of toluene and 100 ml of water are added. The mixture is stirred and 13.6 g of K$_2$CO$_3$ are slowly added. The organic layer is separated off, washed with water, dried under sodium sulfate, filtered and evaporated under vacuum. The product obtained is a white powder.

Melting point: 60° C.

EXAMPLE 12

Preparation of the Compound of the Formula

[Chemical structure: bis-piperidinone compound with H—N and N—H termini connected via cyclohexyl-CH$_2$-cyclohexyl linker, each piperidinone ring bearing gem-dimethyl groups and a carbonyl]

Using the appropriate starting materials, the preparation is carried out in analogy to the method described in EXAMPLE 10. The product obtained is a white powder.

Melting point: 160° C.

EXAMPLE 13

Preparation of the Compound of the Formula

[Chemical structure: bis-piperidinone compound with N—CH$_3$ termini connected via cyclohexyl-CH$_2$-cyclohexyl linker, each piperidinone ring bearing gem-dimethyl groups and a carbonyl]

The compound is prepared following the procedure described in EXAMPLE 11 and using the compound of EXAMPLE 12 as starting material. The product obtained is a white powder.

Melting point: 185° C.

EXAMPLE 14

Preparation of the Compound of the Formula

[Chemical structure: bis-piperidinone compound with N—C(O)—CH=CH$_2$ (acryloyl) termini connected via cyclohexyl-CH$_2$-cyclohexyl linker, each piperidinone ring bearing gem-dimethyl groups and a carbonyl]

A solution of 11.7 ml (0.12 mol) of acryloyl choride in 50 ml of dichloromethane is slowly added to a solution of 30 g (0.06 mol) of the compound of EXAMPLE 12 and 12.4 ml (0.12 mol) of triethylamine in 250 ml of dichloromethane, cooled to 0° C. After the addition, the mixture is allowed to react for 1 hour at 0° C. Then, the mixture is heated to room temperature and left to react for 4 hours. Subsequently, the mixture is filtered and washed three times with water and the organic layer is separated off, dried over sodium sulfate and evaporated under vacuum. The product obtained is a white powder.

Melting point: 208° C.

Example I-1

Light Stabilizing Action in Polypropylene Tapes 1 g of each of the compounds listed in Table I-1, 1 g of tris[2,4-di-tert-butylphenyl] phosphite, 0.5 g of pentaerythritol tetrakis[3-(3,5-di-tert-butyl-4-hydroxyphenyl)propionate] and 1 g of calcium stearate are mixed in a turbomixer with 1000 g of polypropylene powder (PP ®MOPLEN S SF) having a melt index of 3.7 (measured at 230° C. and 2.16 Kg).

The mixtures are extruded at 200–220° C. to give polymer granules which are subsequently converted to stretched tapes of 50 µm thickness and 2.5 mm width, using a semi-industrial type of apparatus (®Leonard-Sumirago (VA)-Italy) and working under the following conditions:

| | |
|---|---|
| Extruder temperature: | 210–230° C. |
| Head temperature: | 240–260° C. |
| Stretch ratio: | 1:6 |

The tapes thus prepared are mounted on a white card and exposed in a Weather-O-Meter ®Atlas Ci 65 (ASTM G 26-96) with a black panel temperature of 63° C.

The residual tenacity is measured, by means of a constant velocity tensometer, on a sample taken after various light exposure times; from this, the exposure time (in hours) required to halve the initial tenacity ($T_{50}$) is measured.

By way of comparison, tapes prepared under the same conditions as indicated above, but without the addition of the stabilizers of the present invention, are exposed.

The results obtained are shown in Table I-1.

TABLE I-1

| Stabilizer | $T_{50}$ (hours) |
|---|---|
| Without stabilizer | 520 |
| Compound of EXAMPLE 3C | 2750 |
| Compound of EXAMPLE 4 | 3090 |
| Compound of EXAMPLE 7 | 3210 |
| Compound of EXAMPLE 8B | 2750 |
| Compound of EXAMPLE 9 | 2690 |

The above results show that the compounds of this invention are effective light stabilizers.

Example I-2

Light Stabilizing Action in Polypropylene Fibres 2.5 g of each of the compounds listed in Table I-2, 1 g of tris(2,4-di-t-butylphenyl) phosphite, 1 g of calcium monoethyl 3,5-di-t-butyl-4-hydroxybenzyl-phosphonate, 1 g of calcium stearate and 2.5 g of titanium dioxide are mixed in a slow mixer with 1000 g of polypropylene powder (PP ®MOPLEN FLF 20) having a melt index=12.2 g/10 min (measured at 230° C. and 2.16 kg).

The mixtures are extruded at 200°–230° C. to obtain polymer granules which are then converted into fibres using a semi-industrial apparatus (®Leonard-Sumirago(VA), Italy) and operating under the following conditions:

| | |
|---|---|
| Extruder temperature: | 230–245° C. |
| Head temperature: | 255–260° C. |
| Draw ratio: | 1:3.5 |
| Linear density: | 11 dtex per filament |

The fibres prepared in this way are exposed, after mounting on white cardboard, in an ®Atlas Ci 65 Weather-C-Meter (ASTM G 26-96) with a black panel temperature of 63° C.

For samples taken after various times of exposure to the light, the residual tenacity is measured using a constant-speed tensometer, and the exposure time in hours needed to halve the initial tenacity ($T_{50}$) is then calculated.

For purposes of comparison, fibres prepared under the same conditions as stated above, but without adding the stabilizers of the present invention, are also exposed.

The results are shown in Table I-2.

Table I-2

| Stabilizer | $T_{50}$ (hours) |
|---|---|
| Without stabilizer | 310 |
| Compound of EXAMPLE 3C | 2830 |
| Compound of EXAMPLE 4 | 2710 |
| Compound of EXAMPLE 7 | 2830 |
| Compound of EXAMPLE 8B | 2170 |
| Compound of EXAMPLE 9 | 2510 |

The above results show that the compounds of this invention are effective light stabilizers.

Example I-3

Stabilization of Polyethylene Films, Treated or Untreated with Pesticides 2.1 g of the compound of EXAMPLE 9 are mixed with 700 g of low density polyethylene (LDPE) pellets (Riblene® FF 29 supplied by ®ENICHEM, Milano, Italy; density: 0.921 g/cm$^3$; melt flow index at 190° C. and 2.16 kg: 0.62 g/10 min) in a turbo mixer.

The mixture is extruded at a maximum temperature of 200° C. Films of 150 μm thickness are obtained by compression molding (3 min at 170° C.), containing 0.3% of the compound of EXAMPLE 9.

Some of the films are treated with pesticides as follows:

The films are stored before Weather-O-Meter exposure for 20 days in a dryer at 30° C. over a concentrated solution of VAPAM® in water (1:1 ratio in parts by volume) without direct contact with the solution. (VAPAM® (®BASLINI SpA, Treviglio/BG, Italy) is an aqueous solution of 382 g per liter of metam-sodium having the formula CH$_3$-NH-CS-SNa.)

After the above treatment, film samples are exposed in quartz tubes in a Weather-O-Meter ®Atlas Ci 65 with a black panel temperature of 63° C. Untreated films are exposed as well under the same conditions. The degradation process is monitored by measuring the increase of carbonyl in the sample with a Fourier Transform Infrared Spectrophotometer. A high increase of carbonyl indicates high degradation. The results are listed in Table I-3.

Table I-3

| Stabilizer | Non treated Hours to carbonyl increase of 0.1 | Pesticide treated Hours to carbonyl increase of 0.3 |
|---|---|---|
| Without stabilizer | 610 | 400 |
| Compound of EXAMPLE 9 | 5380 | 3560 |

The above results show that the compounds of this invention are effective light stabilizers for polyolefin which is in contact with a pesticide.

Example II-1

Stabilization of a Gray Pigmented polycarbonate/acrylonitrile-butadiene-styrene (PC/ABS) Blend A commercial PC/ABS blend (®Cycoloy MC 8002) pigmented with 1% by weight of ®Gray 9779 from Uniform Color Company is stabilized by addition of 1% by weight of 2-(2'-hydroxy-3',5'-bis(1",1"-dimethylbenzyl)phenyl)benzotriazole and 0.5% by weight of the compound indicated in Table II-1. A sample containing only the 1% by weight of the benzotriazole stabilizer and an unstabilized sample—both containing 1% by weight of gray pigment—serve as comparison.

Izod bars (2.5"L×0.5"W×0.125"W) are prepared by injection molding on a ®BOY 30 machine, barrel temperature 246°–268° C., die temperature 268° C. Accelerated weathering is performed using an ®Atlas Ci65A Weather-O-meter (XAW), operating in "Dry XAW" mode (ASTM G26-90, method C). After regular intervals, the color change ΔE according to DIN 6174 is determined. The results are listed in Table II-1.

TABLE II-1

| Irradiation time:<br>Stabilizer | 249.8 hours<br>ΔE | 750 hours<br>ΔE |
|---|---|---|
| None | 3.3 | 9.0 |
| Benzotriazole stabilizer*) | 1.7 | 6.7 |
| Compound of EXAMPLE 5 | 0.8 | 5.5 |
| Compound of EXAMPLE 8B | 0.7 | 5.6 |

*)2-(2'-hydroxy-3',5'-bis(1",1"-dimethylbenzyl)phenyl)benzotriazole

The PC/ABS samples stabilized according to this invention show an excellent color stability.

Example II-2

Stabilization of a White Pigmented polycarbonate/acrylonitrile-butadiene-styrene (PC/ABS) Blend Samples are prepared from a commercial PC/ABS blend (®Cycoloy MC 8002) as described in EXAMPLE II-1 except that TiO$_2$ (® Tiona RCL-4 rutile; ®SCM chemicals) is used as pigment. Weathering and assessment is carried out as described in EXAMPLE II-1. The results are shown in Table II-2.

TABLE II-2

| Irradiation time:<br>Stabilizer | 249.6 hours<br>ΔE | 749.3 hours<br>ΔE | 999.8 hours<br>ΔE |
|---|---|---|---|
| None | 4.6 | 15.4 | 21.8 |
| Benzotriazole stabilizer*) | 2.8 | 9.5 | 15.7 |
| Compound of EXAMPLE 5 | 4.8 | 4.8 | 10.2 |
| Compound of EXAMPLE 8B | 4.3 | 6.1 | 11.2 |

*)2-(2'-hydroxy-3',5'-bis(1",1"-dimethylbenzyl)phenyl)benzotriazole

The PC/ABS samples stabilized according to this invention show an excellent color stability, particularly at prolonged exposure intervals.

Abbreviations Used in the Following EXAMPLES III-1 to III-7

Coup Y1: Compound of the formula

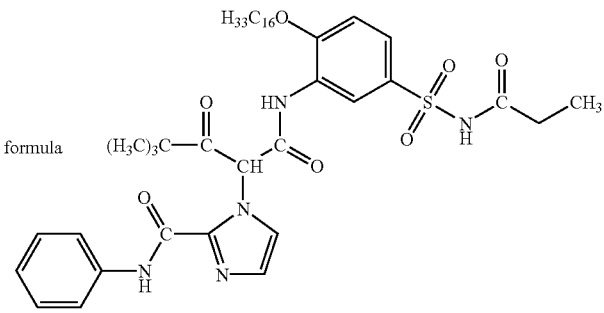

Coup Y2: Compound of the formula

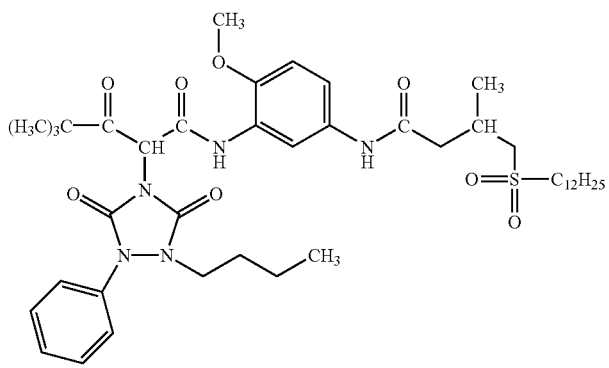

-continued
Coup Y3: Compound of the formula 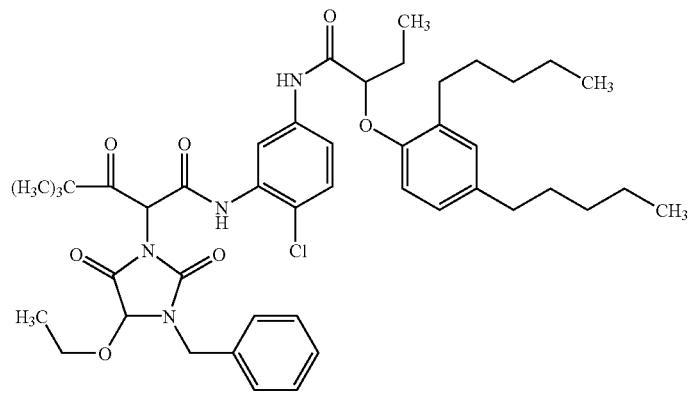
Coup Y4: Compound of the formula 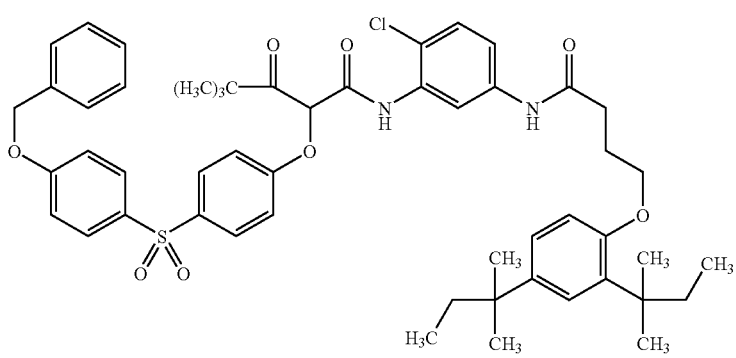
Solv1: Compound of the formula 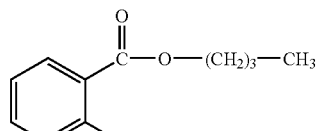
Hal: Compound of the formula 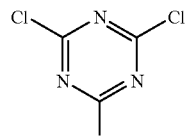
Sul: Compound of the formula 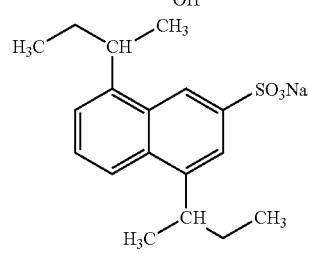
Coadd 1: Compound of the formula 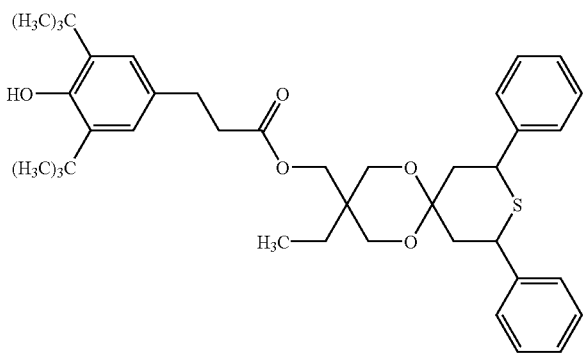

Coadd 2: Compound of the formula 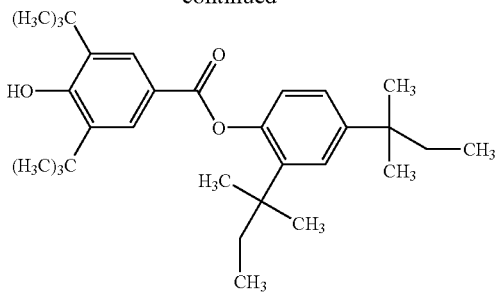

Example III-1

Stabilization of Photographic Layers

Chromogenic photographic layers are prepared by hand-coating a gelatine emulsion containing silver bromide, yellow coupler and an additive of this invention on a polyethylene-coated paper.

The composition of the layer is as given in the following table (amounts are in mg/m²).

| Component | Amount in the layer |
|---|---|
| Gelatine | 5150 |
| AgBr | 520 |
| Yellow coupler CoupY2 | 854 |
| Coupler solvent Solv1 | 285 |
| Additive (Table III-1) | 256 |
| Hardener Ha1 | 300 |
| Surfactant Su1 | 340 |

The layers are dried for 7 days in a ventilated cabinet. The dried samples are exposed to white light through a step-wedge of 0.3 logE exposure steps. They are developed with the P94 process for negative colour paper from ®Agfa-Gevaert, following the manufacturer's recommendations.

After exposure and processing, the remission density of the yellow dye is measured in the blue channel. The results are listed in Table III-1.

TABLE III-1

| Additive | 100 × $D_{max}$ |
|---|---|
| None | 176 |
| Compound of EXAMPLE 7 | 209 |

These results show that the compounds of the present invention improve the maximal dye yield.

Example III-2

Stabilization of Photographic Layers

Chromogenic photographic layers are prepared by hand-coating a gelatine emulsion containing silver bromide, yellow coupler and an additive of this invention on a polyethylene-coated paper.

The composition of the layer is as given in the following table (amounts are in mg/m²).

| Component | Amount in the layer |
|---|---|
| Gelatine | 5150 |
| AgBr | 520 |
| Yellow coupler CoupY1 | 835 |
| Coupler solvent Solv1 | 278 |
| Additive (Table III-2) | 250 |
| Hardener Ha1 | 300 |
| Surfactant Su1 | 340 |

The layers are dried for 7 days in a ventilated cabinet. The dried samples are exposed to white light through a step-wedge of 0.3 logE exposure steps. They are developed with the P94 process for negative colour paper from ®Agfa-Gevaert, following the manufacturer's recommendations.

After exposure and processing, the remission density of the yellow dye is measured in the blue channel. The samples are then exposed in an ®Atlas weather-O-meter so as to receive 60 kJ/cm² light energy. The temperature is 43° C. and the relative humidity is 50%. The density loss (−ΔD) starting from a blue-density of 1 (OD=1) is determined. The results are listed in Table III-2.

TABLE III-2

| Additive | −ΔD(60 kJ/cm², from OD = 1) |
|---|---|
| None | 55 |
| Compound of EXAMPLE 1C | 29 |
| Compound of EXAMPLE 3C | 26 |
| Compound of EXAMPLE 7 | 27 |
| Compound of EXAMPLE 8B | 30 |
| Compound of EXAMPLE 9 | 33 |

These results show that the compounds of the present invention improve the light stability of yellow photographic layers.

Example III-3

Stabilization of Photographic Layers

The procedure described in EXAMPLE III-2 is repeated using a composition of the layer as given in the following table (amounts are in mg/m²).

| Component | Amount in the layer |
|---|---|
| Gelatine | 5150 |
| AgBr | 520 |

-continued

| Component | Amount in the layer |
|---|---|
| Yellow coupler CoupY2 | 854 |
| Coupler solvent Solv1 | 285 |
| Additive (Table III-3) | 256 |
| Hardener Ha1 | 300 |
| Surfactant Su1 | 340 |

The results are listed in Table III-3.

TABLE III-3

| Additive | $-\Delta D(60\ kJ/cm^2,\ from\ OD = 1)$ |
|---|---|
| None | 47 |
| Compound of EXAMPLE 1C | 23 |
| Compound of EXAMPLE 3C | 23 |
| Compound of EXAMPLE 4 | 27 |
| Compound of EXAMPLE 7 | 25 |
| Compound of EXAMPLE 8B | 21 |
| Compound of EXAMPLE 9 | 27 |

The data show that the compounds of the present invention improve the light stability of yellow photographic layers.

Example III-4

Stabilization of Photographic Layers

The procedure described in EXAMPLE III-2 is repeated using a composition of the layer as given in the following table (amounts are in mg/m$^2$).

| Component | Amount in the layer |
|---|---|
| Gelatine | 5150 |
| AgBr | 520 |
| Yellow coupler CoupY3 | 859 |
| Coupler solvent Solv1 | 286 |
| Additive (Table III-4) | 258 |
| Hardener Ha1 | 300 |
| Surfactant Su1 | 340 |

The results are listed in Table III-4.

TABLE III-4

| Additive | $-\Delta D(60\ kJ/cm^2,\ from\ OD = 1$ |
|---|---|
| None | 32 |
| EXAMPLE 1C | 26 |
| EXAMPLE 3C | 25 |
| EXAMPLE 7 | 23 |
| EXAMPLE 8B | 23 |

The data show that the compounds of the present invention improve the light stability of yellow photographic layers.

Example III-5

Stabilization of Photographic Layers

The procedure described in EXAMPLE III-2 is repeated using a composition of the layer as given in the following table (amounts are in mg/m$^2$).

| Component | Amount in the layer |
|---|---|
| Gelatine | 5150 |
| AgBr | 520 |
| Yellow coupler CoupY4 | 973 |
| Coupler solvent Solv1 | 324 |
| Additive (Table III-5) | 292 |
| Hardener Ha1 | 300 |
| Surfactant Su1 | 340 |

The results are listed in Table III-5.

TABLE III-5

| Additive | $-\Delta D(60\ kJ/cm^2,\ from\ OD = 1)$ |
|---|---|
| None | 41 |
| EXAMPLE 1C | 30 |
| EXAMPLE 3C | 31 |
| EXAMPLE 4 | 34 |
| EXAMPLE 7 | 28 |
| EXAMPLE 8b | 30 |
| EXAMPLE 9 | 31 |

The data show that compounds of the present invention improve the light stability of yellow photographic layers Example III-6

Stabilization of Photographic Layers.

The procedure described in EXAMPLE III-2 is repeated using a composition of the layer as given in the following table (amounts are in mg/m$^2$).

| Component | Amount in the layer |
|---|---|
| Gelatine | 5150 |
| AgBr | 520 |
| Yellow coupler (Table III-6) | 1.07 mmol/m$^2$ |
| Coupler solvent Solv1 | 33% of the coupler weight/m$^2$ |
| Additive (Table III-6) | 30% of the coupler weight/m$^2$ |
| Hardener Ha1 | 300 |
| Surfactant Su1 | 340 |

The results are listed in Table III-6

TABLE III-6

| Coupler | Additive | $-\Delta D(60\ kJ/cm^2,\ from\ OD = 1)$ |
|---|---|---|
| CoupY1 | None | 65 |
| CoupY1 | Compound of EXAMPLE 12 | 37 |
| CoupY1 | Compound of EXAMPLE 13 | 36 |
| CoupY1 | Compound of EXAMPLE 14 | 38 |
| CoupY2 | None | 51 |
| CoupY2 | Compound of EXAMPLE 12 | 31 |
| CoupY2 | Compound of EXAMPLE 13 | 28 |
| CoupY2 | Compound of EXAMPLE 14 | 27 |
| CoupY3 | None | 28 |
| CoupY3 | Compound of EXAMPLE 12 | 18 |
| CoupY3 | Compound of EXAMPLE 14 | 18 |
| CoupY4 | None | 22 |
| CoupY4 | Compound of EXAMPLE 14 | 17 |

The data show that compounds of the present invention improve the light stability of yellow photographic layers.

Example III-7

Stabilization of Photographic Layers

The procedure described in EXAMPLE III-2 is repeated using a composition of the layer as given in the following table (amounts are in mg/m$^2$).

| Component | Amount in the layer |
| --- | --- |
| Gelatine | 5150 |
| AgBr | 520 |
| Yellow coupler CoupY1 | 835 mg/m$^2$ |
| Coupler solvent Solv1 | 278 mg/m$^2$ |
| Additive | Table III-7 |
| Co-stabilizer | Table III-7 |
| Hardener Ha1 | 300 |
| Surfactant Su1 | 340 |

The results are listed in Table III-7.

TABLE III-7

| Additive | mg/m$^2$ | Co-stabilizer | mg/m$^2$ | $-\Delta D(60 \text{ kJ/cm}^2,$ from OD = 1) |
| --- | --- | --- | --- | --- |
| None | | | | 69 |
| — | | Coadd1 | 250 | 42 |
| Compound of EXAMPLE 12 | 250 | — | — | 46 |
| Compound of EXAMPLE 12 | 125 | Coadd1 | 125 | 37 |
| — | | Coadd2 | 250 | 48 |
| Compound of EXAMPLE 12 | 125 | Coadd2 | 125 | 34 |

The previous results show that additives of the present invention improve the efficiency of classical stabilizers used in yellow photographic layers.

Good results are also achieved, when using the yellow coupler CoupY2 instead of the yellow coupler CoupY1.

Example IV-1

Measuring the Discolouration of Cured Powder Coatings Based on a Carboxy-Functional Polyester with ®Araidit PT910

A powder coating composition (see Table IV-1-a) is prepared by mixing the different components, with the exception of the stabilizer, and extruding the mixture using a ®Buss PLK46L type extruder at 40° C. (screw and zone 1) and at 100° C. (zone 2) at 125 rpm. The melting temperature in the extruder is about 96° C. The powder coating composition is then ground to an average particle size of about 51 µm. Instead of spraying the formulation dry as powder coating, it is dissolved or dispersed in a solvent mixture (see Table IV-1-b) together with the corresponding amount of stabilizer and is then applied to a white aluminium coil coat sheet using a 150 µm casting knife.

TABLE IV-1-a

| | Sample (amounts in gram) | |
| --- | --- | --- |
| Components Sample | 1) | 2) to 3) |
| ® Alftalat 9936/A$^{a)}$ | 893 | 893 |
| ® Araldit PT910$^{b)}$ | 83 | 83 |
| ® Resiflow PV88 | 20 | 20 |
| Benzoin | 4 | 4 |
| Titanium dioxide type 2160$^{c)}$ | 500 | 500 |
| Stabilizer (see Table IV-1-c) | 0 | 8.93 |
| Total: | 1500 | 1508.9 |

$^{a)}$Carboxy-functional polyester of ® Vianova Resins S.p.A., Italy.
$^{b)}$Araldit PT910 is an epoxy crosslinker, of ® Ciba Specialty Chemicals, Basel, Switzerland
$^{c)}$TiO$_2$, of ® Kronos Titan International, Leverkusen, Germany.

TABLE IV-1-b

| Components | Amounts |
| --- | --- |
| Dry acetone/dichloromethane 4:1 v/v | 541 g |
| ® Byk 300$^{d)}$ | 7 g |
| ® Fluorad FC170C$^{e)}$ | 2 g |
| Powder coating composition (acc. to Table IV-1-a) | 450 g |

$^{d)}$® Byk 300 is an anticratering agent based on dimethylpolysiloxane, of ® Byk Chemie, D-4230 Wesel, Germany.
$^{e)}$® Fluorad FC170C is a nonionic fluorinated alkylpolyoxyethylene ethanol crosslinker, of ® 3M Industrial Chemical Products Division, St. Paul, MN 55144-1000, U.S.A.

After a 48 hour drying time, the coatings are stoved in an electric furnace. The chosen oven temperatures and stoving times correspond in practice to severe overbaking conditions. The colour after stoving is measured using a spectrophotometer according to DIN 6174, taking b* as measure of the yellowing. High b* values denote severe yellowing. The results are compiled in Table IV-1-c.

TABLE IV-1-c

| Sample | Stabilizer | Colour after stoving in an electric furnace (b*) for 90 min at 180° C. |
| --- | --- | --- |
| 1) | none | 2.52 |
| 2) | Compound of EXAMPLE 3C | 2.20 |
| 3) | Compound of EXAMPLE 9 | 2.16 |

The invention claimed is:

1. A compound of the formula (I)

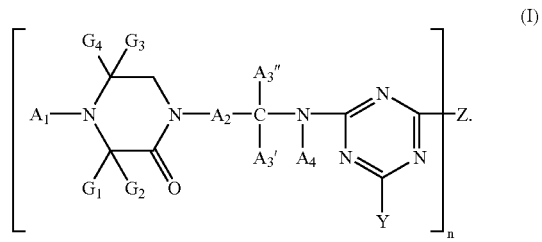

wherein
n is 4;
$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

$A_1$ is hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl by 1, 2 or 3 $C_1$–$C_4$alkyl or $C_1$–$C_4$alkoxy; $C_1$–$C_8$acyl, $C_1$–$C_{18}$alkoxy, $C_5$–$C_{12}$cycloalkoxy, $C_7$–$C_{12}$phenylalkoxy unsubstituted or substituted on the phenyl by 1, 2 or 3 $C_1$–$C_4$alkyl or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl;

$A_2$ is $C_2$–$C_{14}$alkylene or a group —CA$_2'$(A$_2''$)— with $A_2'$ and $A_2''$ being independently of one another hydrogen, $C_1$–$C_{18}$alkyl or $C_5$–$C_{12}$cycloalkyl;

$A_3'$ and $A_3''$ are independently of one another hydrogen, $C_1$–$C_{18}$alkyl, $C_2$–$C_{18}$alkyl interrupted by oxygen; or $C_5$–$C_{12}$cycloalkyl;

$A_4$ is hydrogen, $C_1$–$C_{18}$alkyl, $C_2$–$C_{18}$hydroxyalkyl, $C_3$–$C_{18}$alkenyl, $C_5$–$C_{12}$cycloalkyl which is unsubstituted or substituted by 1, 2 or 3 $C_1$–$C_4$alkyl; $C_7$–$C_{12}$phenylalkyl which is unsubstituted or substituted on the phenyl by 1, 2 or 3 $C_1$–$C_4$alkyl; tetrahydrofurfuryl, a group of the formula (II),

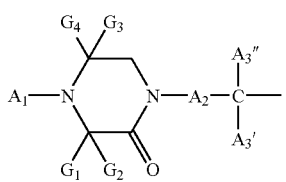

wherein $A_1$, $A_2$, $A_3'$ and $A_3''$ are as defined above;

or $C_2$–$C_4$alkyl which is substituted in the 2, 3 or 4 position by $C_1$–$C_8$alkoxy, di($C_1$–$C_4$alkyl)amino or a group of the formula (III);

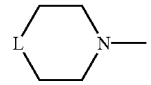

with L being —O—, —CH$_2$—, —CH$_2$CH$_2$— or >N—CH$_3$;

Y is —OA$_5$, —SA$_5$, —N(A$_6$)(A$_7$) or a group of the formula (IV);

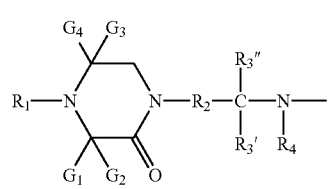

wherein $R_1$ has one of the definitions given above for $A_1$, $R_2$ has one of the definitions given above for $A_2$, $R_3'$ and $R_3''$ have independently of one another one of the definitions given above for $A_3'$ and $A_3''$, and $R_4$ has one of the definitions given above for $A_4$;

$A_5$, $A_6$ and $A_7$ are independently of one another hydrogen, $C_1$–$C_{18}$alkyl, $C_3$–$C_{18}$alkenyl, $C_5$–$C_{12}$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_{12}$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by $C_1$–$C_8$alkoxy, di($C_1$–$C_4$alkyl)amino or a group of the formula (III), and $A_5$ is additionally a group of the formula (II), or —N(A$_6$)(A$_7$) is additionally a group of the formula (III);

Z is a group of the formula (VII)

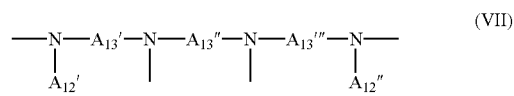

wherein $A_{12}'$ and $A_{12}''$ are independently of one another hydrogen, $C_1$–$C_{18}$alkyl, $C_3$–$C_{18}$alkenyl, $C_5$–$C_{12}$cycloalkyl which is unsubstituted or substituted by 1, 2, or 3 $C_1$–$C_4$alkyl; $C_7$–$C_{12}$phenylalkyl which is unsubstituted or substituted on the phenyl by 1, 2, 3 $C_1$–$C_4$alkyl; tetrahydrofurfuryl, a group of the formula (II) or $C_2$–$C_4$alkyl which is substituted in the 2, 3 or 4 position by -OH, $C_1$–$C_8$alkoxy, di($C_1$–$C_4$alkyl)amino or a group of the formula (III); and $A_{13}'$, $A_{13}''$ and $A_{13}'''$ are independently of one another $C_2$–$C_{14}$alkylene, $C_4$–$C_{14}$alkylene interrupted by oxygen or sulfur; $C_5$–$C_7$cycloalkylene, $C_5$–$C_7$cycloalkylenedi($C_1$–$C_4$alkylene), $C_1$–$C_4$alkylenedi($C_5$–$C_7$cycloalkylene) or phenylenedi ($C_1$–$C_4$alkylene);

the radicals $A_1$, the radicals $A_2$, the radicals $A_3'$, the radicals $A_3''$, the radicals $A_4$ or the radicals Y have independently of one another the same meaning or a different meaning and the repeating units of the formula

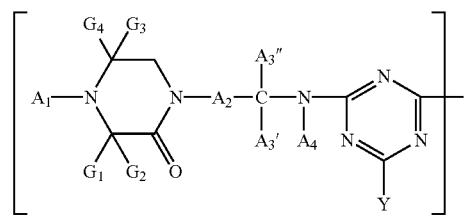

being present in the compound of the formula (I) are identical or different;

with the proviso that in at least one group of the formula

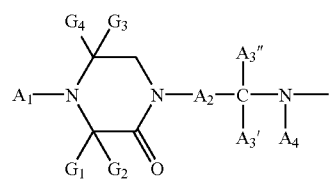

$A_4$ is different from hydrogen and -(A$_3'$)C(A$_3''$)- is different from methylene.

2. A compound according to claim 1 wherein
the radicals $A_1$ are independently of one another hydrogen, $C_1$–$C_4$alkyl, —OH, allyl, $C_1$–$C_{12}$alkoxy, $C_5$–$C_8$cycloalkoxy, benzyl, acetyl or acryloyl.

3. A compound according to claim 1 wherein
$G_1$, $G_2$, $G_3$ and $G_4$ are independently of one another $C_1$–$C_4$alkyl.

4. A compound according to claim 1 wherein
$A_3'$ and $A_3''$ are independently of one another $C_1$–$C_{18}$alkyl, $C_2$–$C_{18}$alkyl interrupted by oxygen; or $C_5$-$C_{12}$cycloalkyl;
$A_4$ and $R_4$ are independently of one another $C_1$–$C_{18}$alkyl, $C_2$–$C_{18}$hydroxyalkyl, $C_3$–$C_{18}$alkenyl, $C_5$-$C_{12}$cycloalkyl which is unsubstituted or substituted by 1, 2 or 3 $C_1$-$C_4$alkyl; $C_7$–$C_{12}$phenylalkyl which is unsubstituted or substituted on the phenyl by 1, 2 or 3 $C_1$–$C_4$alkyl; tetrahydrofurfuryl, a group of the formula (II), or $C_2$–$C_4$alkyl which is substituted in the 2, 3 or 4 position by $C_1$–$C_8$alkoxy, di($C_1$–$C_4$alkyl)amino or a group of the formula (III); and R.4 is additionally hydrogen.

5. A compound according to claim 1 wherein
$G_1$, $G_2$, $G_3$ and $G_4$ are independently of one another $C_1$–$C_6$alkyl or cyclohexyl or the radicals $G_1$ and $G_2$ and the radicals $G_3$ and $G_4$ form independently of one another, together with the carbon atom they are attached to, cyclohexyl;
$A_2$ is $C_2$–$C_{12}$alkylene or a group —$CA_2'(A_2'')$- with $A_2'$ and $A_2''$ being independently of one another hydrogen, $C_1$–$C_8$alkyl or $C_5$–$C_8$cycloalkyl;
$A_3'$ and $A_3''$ are independently of one another hydrogen, $C_1$–$C_8$alkyl, $C_2$–$C_8$alkyl interrupted by oxygen; or $C_5$–$C_8$cycloalkyl;
$A_4$ is hydrogen, $C_1$–$C_{12}$alkyl, $C_2$–$C_{12}$hydroxyalkyl, $C_3$–$C_{12}$alkenyl, $C_5$–$C_8$cycloalkyl which is unsubstituted or substituted by 1, 2 or 3 $C_1$–$C_4$alkyl; $C_7$–$C_9$phenylalkyl which is unsubstituted or substituted on the phenyl by 1, 2 or 3 $C_1$–$C_4$alkyl; tetrahydrofurfuryl, a group of the formula (II) or $C_2$–$C_4$alkyl which is substituted in the 2, 3 or 4 position by $C_1$–$C_4$alkoxy, di($C_1$–$C_4$alkyl)amino or a group of the formula (III);
Y is —$OA_5$, —$N(A_6)(A_7)$ or a group of the formula (IV);
$A_5$, $A_6$ and $A_7$ are independently of one another hydrogen, $C_1$–$C_{12}$alkyl, $C_3$–$C_{12}$alkenyl, $C_5$–$C_8$cycloalkyl which is unsubstituted or substituted by 1, 2 or 3 $C_1$–$C_4$alkyl; phenyl which is unsubstituted or substituted by 1, 2 or 3 $C_1$–$C_4$alkyl or $C_1$–$C_4$alkoxy; $C_7$–$C_9$phenylalkyl which is unsubstituted or substituted on the phenyl by 1, 2 or 3 $C_1$–$C_4$alkyl; tetrahydrofurfuryl or $C_2$–$C_4$alkyl which is substituted in the 2, 3 or 4 position by $C_1$–$C_4$alkoxy, di($C_1$–$C_4$alkyl)amino or a group of the formula (III);
or —$N(A_4)(A_7)$ is additionally a group of the formula (III); wherein $A_{12}'$ and $A_{12}''$are independently of one another hydrogen, $C_1$–$C_{12}$alkyl, $C_3$–$C_{12}$alkenyl, $C_5$–$C_8$cycloalkyl which is unsubstituted or substituted by 1, 2, or 3 $C_1$–$C_4$alkyl; tetrahydrofurfuryl, a group of the formula (II) or $C_2$–$C_4$alkyl which is substituted in the 2, 3 or 4 position by –OH, $C_1$–$C_4$alkoxy, di($C_1$–$C_4$alkyl)amino or a group of the formula (III);
$A_{13}'$, $A_{13}''$ and $A_{13}\Delta$ are independently of one another $C_4$–$C_{12}$alkylene, $C_{4-12}$alkylene interrupted by oxygen; $C_5$–$C_7$cycloalkylene, $C_5$–$C_7$cycloalkylenedi($C_1$–$C_4$alkylene), $C_1$–$C_4$alkylenedi($C_5$–$C_7$cyclohexylene) or phenylenedi($C_1$–$C_4$alkylene).

6. A compound according to claim 1 wherein
$G_1$, $G_2$, $G_3$ and $G_4$ are independently of one another $C_1$–$C_4$alkyl;
$A_2$ is $C_2$–$C_{10}$alkylene;
$A_3'$ and $A_3''$ are independently of one another $C_1$–$C_8$alkyl;
$A_4$ is hydrogen, $C_1$–$C_{10}$alkyl, $C_2$–$C_{10}$hydroxyalkyl, $C_3$–$C_{10}$alkenyl, cyclohexyl; benzyl; tetrahydrofurfuryl, a group of the formula (II) or $C_2$–$C_4$alkyl which is substituted in the 2, 3 or 4 position by methoxy, ethoxy, dimethylamino, diethylamino or a group of the formula (III);
Y is —$N(A_6)(A_7)$ or a group of the formula (IV);
$A_6$ and $A_7$ are independently of one another hydrogen, $C_1$–$C_{10}$alkyl, $C_3$–$C_{10}$alkenyl, cyclohexyl; phenyl; benzyl; tetrahydrofurfuryl or $C_2$–$C_4$alkyl which is substituted in the 2, 3 or 4 position by methoxy, ethoxy, dimethylamino, diethylamino or a group of the formula (III);
or —$N(A_6)(A_7)$ is additionally a group of the formula (III); wherein
$A_{12}'$ and $A_{12}''$ are independently of one another hydrogen, $C_1$–$C\_hd 10\_1$ alkenyl, Cyclohexyl, benzyl, tetrahydrofurfuryl, a group of the formula (II) or $C_2$–$C_4$alkyl which is substituted in the 2, 3 or 4 position by OH, methoxyl, ethoxyl, dimethylamino, diethylamino or a group of the formula (III);
$A_{13}'$, $A_{13}''$ and $A_{13}\Delta$ are independently of one another $C_4$–$C_{10}$alkylene interrupted by oxygen; cyclohexylene, cyclohexylenedi($C_1$–$C_4$alkylene), $C_1$–$C_4$alkylenedi($C_5$–$C_7$cyclohexylene) or phenylenedi($C_1$–$C_4$alkylene.

7. A compound according to claim 1 wherein
$G_1$, $G_2$, $G_3$ and $G_4$ are independently of one another $C_1$–$C_4$alkyl;
$A_1$ is hydrogen or $C_1$–$C_4$alkyl;
$A_2$ is $C_2$–$C_{10}$alkylene;
$A_3'$ and $A_3''$ are independently of one another $C_1$–$C_8$alkyl;
$A_4$ is $C_1$–$C_8$alkyl, $C_2$–$C_8$hydroxyalkyl, $C_3$–$C_8$alkenyl, cyclohexyl; benzyl; tetrahydrofurfuryl or a group the formula (II);
Y is —$N(A_6)(A_7)$ or a group of the formula (IV) wherein $R_1$ is hydrogen or $C_1$–$C_4$alkyl, $R_2$ is $C_2$–$C_{10}$alkylene; $R_3'$ and $R_3''$ are independently of one another $C_1$–$C_8$alkyl, and $R_4$ is hydrogen, $C_1$–$C_8$alkyl, $C_2$–$C_8$hydroxyalkyl, $C_3$–$C_8$alkenyl, cyclohexyl, benzyl, tetrahydrofurfuryl or a group of the formula (II);
$A_6$ and $A_7$ are independently of one another hydrogen, $C_1$–$C_8$alkyl, $C_3$–$C_8$alkenyl, cyclohexyl, phenyl, benzyl or tetrahydrofurfuryl;
or —$N(A_6)(A_7)$ is additionally a group of the formula (III) with L being —O—;
Z is a group of the formula (VII) and $A_{13}'$, $A_{13}''$ and $A_{13}''$ are independently of one another $C_2$–$C_{10}$alkylene.

8. A composition containing an organic material susceptible to degradation induced by light, heat or oxidation and at least one compound of the formula (I) according to claim 1.

9. A composition according to claim 8 wherein the organic material is a synthetic polymer.

10. A composition according to claim 8 wherein the organic material is a thermoplastic rubber.

11. A composition according to claim 8 wherein the organic material is a polyolefin.

12. A method for stabilizing an organic material against degradation induced by light, heat or oxidation, which comprises incorporating into said organic material at least one compound according to claim 1.

* * * * *